US011555207B2

(12) United States Patent
Townes et al.

(10) Patent No.: US 11,555,207 B2
(45) Date of Patent: Jan. 17, 2023

(54) CRISPR/CAS9 COMPLEX FOR INTRODUCING A FUNCTIONAL POLYPEPTIDE INTO CELLS OF BLOOD CELL LINEAGE

(71) Applicant: THE UAB RESEARCH FOUNDATION, Birmingham, AL (US)

(72) Inventors: Tim Townes, Birmingham, AL (US); Lei Ding, Vestavia, AL (US); Chia-Wei Chang, San Diego, CA (US)

(73) Assignee: THE UAB RESEARCH FOUNDATION, Birmingham, AL (US)

(*) Notice: Subject to any disclaimer, the term of this patent is extended or adjusted under 35 U.S.C. 154(b) by 325 days.

(21) Appl. No.: 15/737,134

(22) PCT Filed: Jun. 17, 2016

(86) PCT No.: PCT/US2016/038125
§ 371 (c)(1),
(2) Date: Dec. 15, 2017

(87) PCT Pub. No.: WO2016/205680
PCT Pub. Date: Dec. 22, 2016

(65) Prior Publication Data
US 2019/0032089 A1 Jan. 31, 2019

Related U.S. Application Data

(60) Provisional application No. 62/181,145, filed on Jun. 17, 2015.

(51) Int. Cl.
C12N 15/85 (2006.01)
C12N 15/90 (2006.01)
C12N 9/22 (2006.01)
C12N 15/11 (2006.01)
C12N 5/0735 (2010.01)
C12N 5/0789 (2010.01)
C12N 5/0775 (2010.01)
A61P 7/06 (2006.01)
C12N 5/0783 (2010.01)
C12N 5/074 (2010.01)

(52) U.S. Cl.
CPC ............ *C12N 15/907* (2013.01); *A61P 7/06* (2018.01); *C12N 5/0606* (2013.01); *C12N 5/0636* (2013.01); *C12N 5/0647* (2013.01); *C12N 5/0662* (2013.01); *C12N 5/0696* (2013.01); *C12N 9/22* (2013.01); *C12N 15/11* (2013.01); *C12N 15/111* (2013.01); *C12Y 301/00* (2013.01); *C07K 2319/00* (2013.01); *C07K 2319/10* (2013.01); *C07K 2319/21* (2013.01); *C07K 2319/60* (2013.01); *C12N 2310/20* (2017.05); *C12N 2506/45* (2013.01); *C12N 2740/16043* (2013.01); *C12N 2800/80* (2013.01)

(58) Field of Classification Search
CPC .. C12N 5/0606; C12N 5/0662; C12N 5/0696; C12N 5/0647; C12N 15/907; C12N 2800/80; C12N 2310/20
See application file for complete search history.

(56) References Cited

U.S. PATENT DOCUMENTS

| | | | |
|---|---|---|---|
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |
| 8,999,641 B2 | 4/2015 | Zhang et al. | |
| 9,526,784 B2 | 12/2016 | Liu et al. | |
| 9,737,604 B2 | 8/2017 | Liu et al. | |
| 9,822,370 B2 | 11/2017 | Musunuru et al. | |
| 10,208,319 B2 | 2/2019 | Musunuru et al. | |
| 10,266,850 B2 | 4/2019 | Doudna et al. | |
| 2011/0052554 A1* | 3/2011 | Zakrzewski | C07K 14/705 424/93.71 |
| 2012/0100569 A1* | 4/2012 | Liu | C12N 5/0602 435/29 |
| 2014/0120622 A1 | 5/2014 | Gregory et al. | |
| 2015/0071889 A1* | 3/2015 | Musunuru | A61P 35/00 424/93.7 |
| 2015/0071903 A1 | 3/2015 | Liu et al. | |
| 2015/0071906 A1 | 3/2015 | Liu et al. | |

(Continued)

FOREIGN PATENT DOCUMENTS

| | | |
|---|---|---|
| CN | 104894068 A | 9/2015 |
| EP | 2836226 | 10/2017 |

(Continued)

OTHER PUBLICATIONS

Aiuti et al., Gene Therapy for Immunodeficiency Due to Adenosine Deaminase Deficiency, The New England Journal of Medicine, vol. 360, No. 5, Jan. 29, 2009, pp. 447-458.

Aluigi et al., Nucleofection is an Efficient Nonviral Transfection Technique for Human Bone Marrow-Derived Mesenchymal Stem Cells, Stem Cells, vol. 24, No. 2, Feb. 2006, pp. 454-461.

Bialk et al., Regulation of Gene Editing Activity Directed by Single-Stranded Oligonucleotides and CRISPR/Cas9 Systems, Plos One, vol. 10, No. 6, Jun. 8, 2015, pp. 1-19.

Biffi et al., Lentiviral Hematopoietic Stem Cell Gene Therapy Benefits Metachromatic Leukodystrophy, Science, vol. 341, No. 6148, Aug. 23, 2015, pp. 1233158-1-1233158-11.

(Continued)

Primary Examiner — Marcia S Noble
(74) Attorney, Agent, or Firm — Kilpatrick Townsend & Stockton LLP

(57) ABSTRACT

Provided herein are CRIS-PR/Cas9 complexes and methods of using same.

15 Claims, 12 Drawing Sheets
Specification includes a Sequence Listing.

(56) References Cited

U.S. PATENT DOCUMENTS

| | | | |
|---|---|---|---|
| 2016/0009813 A1* | 1/2016 | Themeli | A61K 39/0011 424/134.1 |
| 2017/0349914 A1* | 12/2017 | Cox | C12N 15/1082 |
| 2018/0141992 A1* | 5/2018 | Cowan | C07K 14/70539 |

FOREIGN PATENT DOCUMENTS

| | | |
|---|---|---|
| WO | 2014/059173 A2 | 4/2014 |
| WO | 2014/191128 A1 | 12/2014 |
| WO | 2014191128 | 12/2014 |
| WO | 2015/006498 A2 | 1/2015 |
| WO | 2015/035136 A2 | 3/2015 |
| WO | 2016/123578 A1 | 8/2016 |
| WO | 2016/160721 A1 | 10/2016 |
| WO | 2017180989 | 10/2017 |

OTHER PUBLICATIONS

Caignard et al., Mouse ENU Mutagenesis to Understand Immunity to Infection Methods, Selected Examples, and Perspectives, Genes, vol. 5, No. 4, Dec. 2014, pp. 887-925.

Chang et al., Broad T-Cell Receptor Repertoire in T-Lymphocytes Derived from Human Induced Pluripotent Stem Cells, PLoS One, vol. 9, No. 5, May 14, 2014, pp. 1-10.

Chang et al., Polycistronic Lentiviral Vector for "Hit and Run" Reprogramming of Adult Skin Fibroblasts to Induced Pluripotent Stem Cells, Stem Cells, vol. 27, May 2009, pp. 1042-1049.

Cong et al., Multiplex Genome Engineering Using CRISPR/Cas Systems, Science, vol. 339, No. 6121, Feb. 15, 2013, pp. 819-823.

Davydov et al., Identifying a High Fraction of the Human Genome to be under Selective Constraint Using GERP++, PLoS Computational Biology, vol. 6, No. 12, Dec. 2010, 13 pages.

De Pooter et al., T-cell Potential and Development in Vitro: The OP9-DL1 Approach, Current Opinion in Immunology, vol. 19, No. 2, Apr. 2007, pp. 163-168.

Dervovic et al., Comparative and Functional Evaluation of in Vitro Generated to Ex Vivo CD8 T Cells, Journal of Immunology, vol. 189, No. 7, Oct. 1, 2012, pp. 3411-3420.

European Application No. 16812542.5, Extended European Search Report dated Dec. 7, 2018, 8 pages.

European Application No. 16812542.5, Office Action dated Dec. 19, 2019, 4 pages.

Eynon et al., Distinct Effects of Jak3 Signaling on αβ and γδ Thymocyte Development, Journal of Immunology, vol. 162, No. 3, Feb. 1, 1999, pp. 1448-1459.

Ferrua et al., Update on Gene Therapy for Adenosine Deaminase-Deficient Severe Combined Immunodeficiency, Current Opinion in Allergy and Clinical Immunology, vol. 10, 2010, pp. 551-556.

Forbes et al., The Catalogue of Somatic Mutations in Cancer (COSMIC), Current Protocols in Human Genetics, Apr. 2008, 32 pages.

Fu et al., High-frequency Off-Target Mutagenesis Induced by CRISPR-Cas Nucleases in Human Cells, Nature Biotechnology, vol. 31, No. 9, Sep. 2013, pp. 822-826.

Girl et al., Utilization of the β and γ Chains of the IL-2 Receptor by the Novel Cytokine IL-15, The EMBO Journal, vol. 13, No. 12, Jun. 15, 1994, pp. 2822-2830.

Hacein-Bey-Abina et al., A Modified γ-Retrovirus Vector for X-Linked Severe Combined Immunodeficiency, The New England journal of medicine, vol. 371, No. 15, Oct. 9, 2014, pp. 1407-1417.

Hacein-Bey-Abina et al., Insertional Oncogenesis in 4 Patients after Retrovirus-mediated Gene Therapy of SCID-X1, The Journal of Clinical Investigation, vol. 118, No. 9, Sep. 2, 2008, pp. 3132-3142.

Hacein-Bey-Abina et al., LMO2-Associated Clonal T Cell Proliferation in Two Patients after Gene Therapy for SCID-X1, Science, vol. 302, No. 5644, Oct. 24, 2003, pp. 415-419.

Hanna et al., Treatment of Sickle Cell Anemia Mouse Model with iPS Cells Generated from Autologous Skin, Science, vol. 318, No. 5858, Dec. 21, 2007, pp. 1920-1923.

Hare et al., An Essential Role for the Il-7 Receptor During Intrathymic Expansion of the Positively Selected Neonatal T Cell Repertoire, Journal of Immunology, vol. 165, No. 5, Sep. 1, 2000, pp. 2410-2414.

Kang et al., Defective Development of γ/δ T Cells in Interleukin 7 Receptor-Deficient Mice is Due to Impaired Expression of T Cell Receptor γ Genes, Journal of Experimental Medicine, vol. 190, No. 7, Oct. 4, 1999, pp. 973-982.

Kondo et al., Bcl-2 Rescues T Lymphopoiesis, but Not B or NK Cell Development, in Common γ Chain—Deficient Mice, Immunity, vol. 7, Jul. 1, 1997, pp. 155-162.

Landrum et al., ClinVar: Public Archive of Relationships Among Sequence Variation and Human Phenotype, Nucleic Acids Research, vol. 42, No. D1, Jan. 1, 2014, pp. D980-D985.

Lenz et al., Nucleoporation of Dendritic Cells: Efficient Gene Transfer by Electroporation Into Human Monocyte-Derived Dendritic Cells, FEBS Letters, vol. 538, Nos. 1-3, Mar. 13, 2003, pp. 149-154.

Li et al., Fast and Accurate Long-Read Alignment with Burrows-Wheeler transform, Bioinformatics, vol. 26, No. 5, Mar. 1, 2010, pp. 589-595.

Li et al, Interleukin-7 Inactivates the Pro-Apoptotic Protein Bad Promoting T Cell Survival, The Journal of biological chemistry, vol. 279, No. 28, Jul. 9, 2004, pp. 29160-29166.

Lin et al., Enhanced Homology-Directed Human Genome Engineering by Controlled Timing of CRISPR/Cas9 Delivery, Elife, vol. 3, No. e04766, Dec. 15, 2014, pp. 1-13.

Maasho et al., Efficient Gene Transfer Into the Human Natural Killer Cell Line, NKL, Using the Amaxa Nucleofection System, Journal of Immunological Methods, vol. 284, No. 1-2, 2004, pp. 133-140.

Makarova et al., Evolution and Cassification of the CRISPR-Cas Sytems, Nature Reviews Microbiology, vol. 9, No. 6, Jun. 2011, pp. 467-477.

Mali et al., RNA-Guided Human Genome Engineering via Cas9, Science, vol. 339, No. 6121, Feb. 15, 2013, pp. 823-826.

McKenna et al., The Genome Analysis Toolkit: a Mapreduce Framework for Analyzing Next-generation DNA Sequencing Data, Genome Research, vol. 20, No. 9, Sep. 2010, pp. 1297-1303.

McNaughton et al., Mammalian Cell Penetration, siRNA Transfection, and DNA Transfection by Supercharged Proteins, Proceedings of the National Academy of Sciences of the United States of America, vol. 106, No. 15, Apr. 14, 2009, pp. 6111-6116.

Nosaka et al., Defective Lymphoid Development in Mice Lacking Jak3, Science, vol. 270, 1995, pp. 800-802.

Notarangelo et al., Mutations in Severe Combined Immune Deficiency (SCID) Due to JAK3 Deficiency, Human Mutation, vol. 18, No. 4, Oct. 2001, pp. 255-263.

Ohnuki et al., Generation and Characterization of Human Induced Pluripotent Stem Cells, Current Protocols in Stem Cell Biology, Chapter 4: Unit 4A.2, Jun. 2009.

Pai et al., Transplantation Outcomes for Severe Combined Immunodeficiency, 2000-2009, The New England Journal of Medicine, vol. 371, Jul. 31, 2014, pp. 434-446.

Park et al., Signaling by Intrathymic Cytokines, Not T Cell Antigen Receptors, Specifies CD8 Lineage Choice and Promotes the Differentiation of Cytotoxic-Lineage T Cells, Nature Immunology, vol. 11, No. 3, Mar. 2010, pp. 257-264.

International Application No. PCT/US2016/038125, International Preliminary Report on Patentability dated Dec. 28, 2017, 7 pages.

International Application No. PCT/US2016/038125, International Search Report and Written Opinion dated Oct. 27, 2016, 10 pages.

Quinlan et al., BEDTools: A Flexible Suite of Utilities for Comparing Genomic Features, Bioinformatics, vol. 26, No. 6, Mar. 15, 2010, pp. 841-842.

Rice et al., EMBOSS: The European Molecular Biology Open Software Suite, Trends in Genetics, vol. 16, No. 6, Jun. 2000, pp. 276-277.

Rothenberg et al., Launching the T-cell-lineage Developmental Programme, Nature Reviews Immunology, vol. 8, No. 1, Jan. 2008, pp. 9-21.

Russell et al., Mutation of Jak3 in a Patient with SCID: Essential Role of Jak3 in Lymphoid Development, Science, vol. 270, No. 5237, Nov. 3, 1995, pp. 797-800.

(56) References Cited

OTHER PUBLICATIONS

Sauer et al., Progress in Gene Therapy for Primary Immunodeficiencies Using Lentiviral Vectors, Current Opinion in Allergy and Clinical Immunology, vol. 14, Dec. 2014, pp. 527-534.
Schmitt et al., Induction of T Cell Development and Establishment of T Cell Competence from Embryonic Stem Cells Differentiated in Vitro, Nature Immunology, vol. 5, No. 4, Apr. 2004, pp. 410-417.
Schmitt et al., Induction of T Cell Development from Hematopoietic Progenitor Cells by delta-like-1 in Vitro, Immunity, vol. 17, No. 6, Dec. 2002, pp. 749-756.
Smith et al., Whole-Genome Sequencing Analysis Reveals High Specificity of CRISPR/Cas9 and TALEN-Based Genome Editing in Human iPSCs, Cell Stem Cell, vol. 15, No. 1, Jul. 3, 2014, pp. 12-13.
Takahashi et al., Efficient Introduction of a Gene into Hematopoietic Cells in S-phase by Electroporation, Experimental Hematology, vol. 19, No. 5, Jun. 1991, Abstract.
Takahashi et al., Induction of Pluripotent Stem Cells from Adult Human Fibroblasts by Defined Factors, Cell, vol. 131, No. 5, Nov. 30, 2007, pp. 861-872.
Takahashi et al., Induction of Pluripotent Stem Cells from Mouse Embryonic and Adult Fibroblast Cultures by Defined Factors, Cell, vol. 126, No. 4, Aug. 25, 2006, pp. 663-676.
Thomis et al., Defects in B Lymphocyte Maturation and T Lymphocyte Activation in Mice Lacking Jak3, Science, vol. 270, No. 5237, Nov. 3, 1995, pp. 794-797.
Timmermans et al., Generation of T Cells from Human Embryonic Stem Cell-Derived Hematopoietic Zones, The Journal of Immunology, vol. 182, No. 11, Jun. 1, 2009, pp. 6879-6888.
Veres et al., Low Incidence of Off-Target Mutations in Individual CRISPR-Cas9 and TALEN Targeted Human Stem Cell Clones Detected by Whole-Genome Sequencing, Cell Stem Cell, vol. 15, No. 1, Jul. 3, 2014, 8 pages.
Von Freeden-Jeffry et al., The Earliest T Lineage-Committed Cells Depend on IL-7 for Bcl-2 Expression and Normal Cell Cycle Progression, Immunity, vol. 7, No. 1, Jul. 1, 1997, pp. 147-154.
Welter et al., The NHGRI GWAS Catalog, A Curated Resource of SNP-Trait Associations, Nucleic Acids Research, vol. 42, Jan. 1, 2014, pp. D1001-D1006.
Wen et al., Jak3 Selectively Regulates Bax and Bcl-2 Expression To Promote T-Cell Development, Molecular and Cellular Biology, vol. 21, No. 2, Jan. 2001, pp. 678-689.
Yu et al., Induced Pluripotent Stem Cell Lines Derived from Human Somatic Cells, Science, vol. 318, No. 5858, Dec. 21, 2007, pp. 1917-1920.
Zou et al., Site-specific Gene Correction of a Point Mutation in Human iPS Cells Derived from an Adult Patient with Sickle Cell Disease, Blood, vol. 118, No. 17, Oct. 27, 2011, pp. 4599-4608.
Zuris et al., Cationic Lipid-Mediated Delivery of Proteins Enables Efficient Protein-Based Genome Editing in Vitro and in Vivo, Nature Biotechnology, vol. 33, No. 1, Jan. 2015, pp. 73-80.
Cronican, et al., "Potent Delivery of Functional Proteins into Mammalian Cells in Vitro and In Vivo Using a Supercharged Protein", ACS Chemical Biology, vol. 5, No. 8, 2010, pp. 747-752.
Nouri F.S., et al., "A Recombinant Biopolymeric Platform for Reliable Evaluation of the Activity of pH-Responsive Amphiphile Fusogenic Peptides", Biomacromolecules, vol. 14, 2013, pp. 2033-2040.
Japanese Patent Application No. 2017-565262, "Office Action" dated Jul. 15, 2020, 16 pages with English translation.
Hale M. et al., High-Efficiency Targeted Introduction of an Anti-CDI9-CAR Into the CCR5 Locus in Primary Human T Cells., Molecular Therapy, vol. 23 Supplement 1 (May 2015), p. S113, 284.
Themeli M. et al., Cell Stem Cell, vol. 16 Issue 4 (Apr. 2015), p. 357-366.
Torikai H. et al., Blood, vol. 119 No. 24 (2012), p. 5697-570.
CN201680044599.6, Office Action, dated Aug. 14, 2020, 35 pages with English Translation.
Themeli, et al., "Generation of tumor-targeted human T lymphocytes from induced pluripotent stem cells for cancer therapy", Nature Biotechnology, vol. 31, No. 10, Oct. 2013, pp. 928-935.
Mansilla-Soto et al., "Repair of the Sickle-cell Disease Mutation in Human Stem Cells Using Crispr/cas9 and Single-Stranded Oligodeoxynucleotides", Molecular Therapy, vol. 23, No. 1, May 2015, S137.
Perez et al., "Establishment of HIV-1 Resistance in CD4+ T Cells by Genome Editing Using Zinc-Finger Nucleases", Nature Biotechnology, vol. 26, No. 7, Jun. 29, 2008, 17 pages.
Sun et al., "Optimized TAL Effector Nucleases (TALENs) for Use in Treatment of Sickle Cell Disease", Molecular BioSystems, vol. 8, Apr. 2020, pp. 1255-1263.
Zuris et al. "Efficient Delivery of Genome-Editing Proteins In Vitro and In Vivo," Nature Biotechnol. 33(1): 73-80 (2015).
Barrangou et al., "CRISPR-Cas Systems: Prokaryotes Upgrade to Adaptive Immunity", Molecular Cell, vol. 54, No. 2, 2014, pp. 234-244.
Ramakrishna et al., "Gene Disruption by Cell-Penetrating Peptide-Mediated Delivery of Cas9 Protein and Guide RNA", Genome Research, vol. 24, No. 6, Jun. 2014, pp. 1020-1027.
Chinese Patent Application No. 201680044599.6, Office Action dated Apr. 13, 2021, 10 pages with English translation.
Japanese Patent Application No. 2017-565262, Office Action dated Jun. 2, 2021, 16 pages with English translation.
EP Application No. 16812542.5, Notice of Decision to Grant, dated Oct. 21, 2021, 2 pages.

* cited by examiner

|  | Colonies examined | PCR positive colonies | % |
|---|---|---|---|
| gRNA #1 | 39 | 9 | 23 |
| gRNA #2 | 45 | 33 | 73.3 |
| gRNA #3 | 16 | 1 | 6.25 |
| gRNA #4 | 9 | 3 | 33.3 |
| gRNA #5 | 3 | 0 | 0 |
| gRNA #6 | 7 | 0 | 0 |
| gRNA #1 + #2 | 14 | 14 | 100 |
| gRNA #3 + #4 | 3 | 0 | 0 |
| gRNA #5 + #6 | 4 | 0 | 0 |

JAK3 patient C1837T     Heterozygous corrected     Homozygous corrected

SEQUENCE LISTING

```
<160> NUMBER OF SEQ IDS: 60

<210> SEQ ID NO 1
<211> LENGTH: 19
<212> TYPE: DNA
<213> ORGANISM: Artificial sequence
<220> FEATURE:
<223> OTHER INFORMATION: Synthetic construct

<400> SEQUENCE: 1
taacggcaga cttctccac                                                    19

<210> SEQ ID NO 2
<211> LENGTH: 103
<212> TYPE: DNA
<213> ORGANISM: Artificial sequence
<220> FEATURE:
<223> OTHER INFORMATION: Synthetic construct

<400> SEQUENCE: 2
gtaacggcag acttctccac gttttagagc tagaaatagc aagttaaaat aaggctagtc        60
cgttatcaac ttgaaaaagt ggcaccgagt cggtgctttt ttt                         103

<210> SEQ ID NO 3
<211> LENGTH: 1671
<212> TYPE: PRT
<213> ORGANISM: Artificial sequence
<220> FEATURE:
<223> OTHER INFORMATION: Synthetic construct

<400> SEQUENCE: 3

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Asp Lys Lys Tyr Ser Ile Gly Leu
        35                  40                  45

Asp Ile Gly Thr Asn Ser Val Gly Trp Ala Val Ile Thr Asp Glu Tyr
```

```
                50                  55                  60
Lys Val Pro Ser Lys Lys Phe Lys Val Leu Gly Asn Thr Asp Arg His
 65                  70                  75                  80

Ser Ile Lys Lys Asn Leu Ile Gly Ala Leu Leu Phe Asp Ser Gly Glu
                     85                  90                  95

Thr Ala Glu Ala Thr Arg Leu Lys Arg Thr Ala Arg Arg Tyr Thr
                100                 105                 110

Arg Arg Lys Asn Arg Ile Cys Tyr Leu Gln Glu Ile Phe Ser Asn Glu
                115                 120                 125

Met Ala Lys Val Asp Asp Ser Phe Phe His Arg Leu Glu Glu Ser Phe
                130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
                180                 185                 190

Ile Tyr Leu Ala Leu Ala His Met Ile Lys Phe Arg Gly His Phe Leu
                195                 200                 205

Ile Glu Gly Asp Leu Asn Pro Asp Asn Ser Asp Val Asp Lys Leu Phe
210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
                260                 265                 270

Lys Asn Gly Leu Phe Gly Asn Leu Ile Ala Leu Ser Leu Gly Leu Thr
                275                 280                 285

Pro Asn Phe Lys Ser Asn Phe Asp Leu Ala Glu Asp Ala Lys Leu Gln
                290                 295                 300

Leu Ser Lys Asp Thr Tyr Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
                340                 345                 350

Lys Ala Pro Leu Ser Ala Ser Met Ile Lys Arg Tyr Asp Glu His His
                355                 360                 365

Gln Asp Leu Thr Leu Leu Lys Ala Leu Val Arg Gln Gln Leu Pro Glu
370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
                420                 425                 430

Asn Arg Glu Asp Leu Leu Arg Lys Gln Arg Thr Phe Asp Asn Gly Ser
                435                 440                 445

Ile Pro His Gln Ile His Leu Gly Glu Leu His Ala Ile Leu Arg Arg
                450                 455                 460

Gln Glu Asp Phe Tyr Pro Phe Leu Lys Asp Asn Arg Glu Lys Ile Glu
465                 470                 475                 480
```

```
Lys Ile Leu Thr Phe Arg Ile Pro Tyr Tyr Val Gly Pro Leu Ala Arg
            485                 490                 495

Gly Asn Ser Arg Phe Ala Trp Met Thr Arg Lys Ser Glu Glu Thr Ile
        500                 505                 510

Thr Pro Trp Asn Phe Glu Glu Val Val Asp Lys Gly Ala Ser Ala Gln
            515                 520                 525

Ser Phe Ile Glu Arg Met Thr Asn Phe Asp Lys Asn Leu Pro Asn Glu
        530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
            565                 570                 575

Ala Phe Leu Ser Gly Glu Gln Lys Lys Ala Ile Val Asp Leu Leu Phe
        580                 585                 590

Lys Thr Asn Arg Lys Val Thr Val Lys Gln Leu Lys Glu Asp Tyr Phe
            595                 600                 605

Lys Lys Ile Glu Cys Phe Asp Ser Val Glu Ile Ser Gly Val Glu Asp
        610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
            645                 650                 655

Asp Ile Val Leu Thr Leu Thr Leu Phe Glu Asp Arg Glu Met Ile Glu
        660                 665                 670

Glu Arg Leu Lys Thr Tyr Ala His Leu Phe Asp Asp Lys Val Met Lys
            675                 680                 685

Gln Leu Lys Arg Arg Arg Tyr Thr Gly Trp Gly Arg Leu Ser Arg Lys
        690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
            725                 730                 735

His Asp Asp Ser Leu Thr Phe Lys Glu Asp Ile Gln Lys Ala Gln Val
        740                 745                 750

Ser Gly Gln Gly Asp Ser Leu His Glu His Ile Ala Asn Leu Ala Gly
            755                 760                 765

Ser Pro Ala Ile Lys Lys Gly Ile Leu Gln Thr Val Lys Val Val Asp
        770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
            805                 810                 815

Arg Glu Arg Met Lys Arg Ile Glu Glu Gly Ile Lys Glu Leu Gly Ser
        820                 825                 830

Gln Ile Leu Lys Glu His Pro Val Glu Asn Thr Gln Leu Gln Asn Glu
            835                 840                 845

Lys Leu Tyr Leu Tyr Tyr Leu Gln Asn Gly Arg Asp Met Tyr Val Asp
        850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
            885                 890                 895
```

-continued

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
    915                 920                 925

Lys Leu Ile Thr Gln Arg Lys Phe Asp Asn Leu Thr Lys Ala Glu Arg
        930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
            980                 985                 990

Lys Val Ile Thr Leu Lys Ser Lys Leu Val Ser Asp Phe Arg Lys Asp
        995                 1000                1005

Phe Gln Phe Tyr Lys Val Arg Glu Ile Asn Asn Tyr His His Ala
    1010            1015                1020

His Asp Ala Tyr Leu Asn Ala Val Val Gly Thr Ala Leu Ile Lys
    1025                1030                1035

Lys Tyr Pro Lys Leu Glu Ser Glu Phe Val Tyr Gly Asp Tyr Lys
    1040                1045                1050

Val Tyr Asp Val Arg Lys Met Ile Ala Lys Ser Glu Gln Glu Ile
    1055                1060                1065

Gly Lys Ala Thr Ala Lys Tyr Phe Phe Tyr Ser Asn Ile Met Asn
    1070                1075                1080

Phe Phe Lys Thr Glu Ile Thr Leu Ala Asn Gly Glu Ile Arg Lys
    1085                1090                1095

Arg Pro Leu Ile Glu Thr Asn Gly Glu Thr Gly Glu Ile Val Trp
    1100                1105                1110

Asp Lys Gly Arg Asp Phe Ala Thr Val Arg Lys Val Leu Ser Met
    1115                1120                1125

Pro Gln Val Asn Ile Val Lys Lys Thr Glu Val Gln Thr Gly Gly
    1130                1135                1140

Phe Ser Lys Glu Ser Ile Leu Pro Lys Arg Asn Ser Asp Lys Leu
    1145                1150                1155

Ile Ala Arg Lys Lys Asp Trp Asp Pro Lys Lys Tyr Gly Gly Phe
    1160                1165                1170

Asp Ser Pro Thr Val Ala Tyr Ser Val Leu Val Val Ala Lys Val
    1175                1180                1185

Glu Lys Gly Lys Ser Lys Lys Leu Lys Ser Val Lys Glu Leu Leu
    1190                1195                1200

Gly Ile Thr Ile Met Glu Arg Ser Ser Phe Glu Lys Asn Pro Ile
    1205                1210                1215

Asp Phe Leu Glu Ala Lys Gly Tyr Lys Glu Val Lys Lys Asp Leu
    1220                1225                1230

Ile Ile Lys Leu Pro Lys Tyr Ser Leu Phe Glu Leu Glu Asn Gly
    1235                1240                1245

Arg Lys Arg Met Leu Ala Ser Ala Gly Glu Leu Gln Lys Gly Asn
    1250                1255                1260

Glu Leu Ala Leu Pro Ser Lys Tyr Val Asn Phe Leu Tyr Leu Ala
    1265                1270                1275

Ser His Tyr Glu Lys Leu Lys Gly Ser Pro Glu Asp Asn Glu Gln
    1280                1285                1290

Lys Gln Leu Phe Val Glu Gln His Lys His Tyr Leu Asp Glu Ile

```
              1295                1300                1305

Ile Glu Gln Ile Ser Glu Phe Ser Lys Arg Val Ile Leu Ala Asp
    1310                1315                1320

Ala Asn Leu Asp Lys Val Leu Ser Ala Tyr Asn Lys His Arg Asp
    1325                1330                1335

Lys Pro Ile Arg Glu Gln Ala Glu Asn Ile Ile His Leu Phe Thr
    1340                1345                1350

Leu Thr Asn Leu Gly Ala Pro Ala Ala Phe Lys Tyr Phe Asp Thr
    1355                1360                1365

Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
    1385                1390                1395

Ile Asp Leu Ser Gln Leu Gly Gly Asp Lys Arg Pro Ala Ala Thr
    1400                1405                1410

Lys Lys Ala Gly Gln Ala Lys Lys Lys Lys Gly Ser Gly Ser Asn
    1415                1420                1425

Gly Ser Ser Gly Ser Ala Ser Lys Gly Glu Arg Leu Phe Arg Gly
    1430                1435                1440

Lys Val Pro Ile Leu Val Glu Leu Lys Gly Asp Val Asn Gly His
    1445                1450                1455

Lys Phe Ser Val Arg Gly Lys Gly Lys Gly Asp Ala Thr Arg Gly
    1460                1465                1470

Lys Leu Thr Leu Lys Phe Ile Cys Thr Thr Gly Lys Leu Pro Val
    1475                1480                1485

Pro Trp Pro Thr Leu Val Thr Thr Leu Thr Tyr Gly Val Gln Cys
    1490                1495                1500

Phe Ser Arg Tyr Pro Lys His Met Lys Arg His Asp Phe Phe Lys
    1505                1510                1515

Ser Ala Met Pro Lys Gly Tyr Val Gln Glu Arg Thr Ile Ser Phe
    1520                1525                1530

Lys Lys Asp Gly Lys Tyr Lys Thr Arg Ala Glu Val Lys Phe Glu
    1535                1540                1545

Gly Arg Thr Leu Val Asn Arg Ile Lys Leu Lys Gly Arg Asp Phe
    1550                1555                1560

Lys Glu Lys Gly Asn Ile Leu Gly His Lys Leu Arg Tyr Asn Phe
    1565                1570                1575

Asn Ser His Lys Val Tyr Ile Thr Ala Asp Lys Arg Lys Asn Gly
    1580                1585                1590

Ile Lys Ala Lys Phe Lys Ile Arg His Asn Val Lys Asp Gly Ser
    1595                1600                1605

Val Gln Leu Ala Asp His Tyr Gln Gln Asn Thr Pro Ile Gly Arg
    1610                1615                1620

Gly Pro Val Leu Leu Pro Arg Asn His Tyr Leu Ser Thr Arg Ser
    1625                1630                1635

Lys Leu Ser Lys Asp Pro Lys Glu Lys Arg Asp His Met Val Leu
    1640                1645                1650

Leu Glu Phe Val Thr Ala Ala Gly Ile Lys His Gly Arg Asp Glu
    1655                1660                1665

Arg Tyr Lys
    1670

<210> SEQ ID NO 4
```

<211> LENGTH: 1720
<212> TYPE: PRT
<213> ORGANISM: Artificial sequence
<220> FEATURE:
<223> OTHER INFORMATION: Synthetic construct

<400> SEQUENCE: 4

```
Tyr Gly Arg Lys Lys Arg Gln Arg Arg Pro Pro Gln Ala Gly
1               5                   10                  15

Gly Ser Met Asp Tyr Lys Asp His Asp Gly Asp Tyr Lys Asp His Asp
            20                  25                  30

Ile Asp Tyr Lys Asp Asp Asp Lys Met Ala Pro Lys Lys Lys Arg
        35                  40                  45

Lys Val Gly Ile His Gly Val Pro Ala Ala Asp Lys Lys Tyr Ser Ile
50                  55                  60

Gly Leu Asp Ile Gly Thr Asn Ser Val Gly Trp Ala Val Ile Thr Asp
65                  70                  75                  80

Glu Tyr Lys Val Pro Ser Lys Lys Phe Lys Val Leu Gly Asn Thr Asp
                85                  90                  95

Arg His Ser Ile Lys Lys Asn Leu Ile Gly Ala Leu Leu Phe Asp Ser
                100                 105                 110

Gly Glu Thr Ala Glu Ala Thr Arg Leu Lys Arg Thr Ala Arg Arg Arg
                115                 120                 125

Tyr Thr Arg Arg Lys Asn Arg Ile Cys Tyr Leu Gln Glu Ile Phe Ser
130                 135                 140

Asn Glu Met Ala Lys Val Asp Asp Ser Phe Phe His Arg Leu Glu Glu
145                 150                 155                 160

Ser Phe Leu Val Glu Glu Asp Lys Lys His Glu Arg His Pro Ile Phe
                165                 170                 175

Gly Asn Ile Val Asp Glu Val Ala Tyr His Glu Lys Tyr Pro Thr Ile
                180                 185                 190

Tyr His Leu Arg Lys Lys Leu Val Asp Ser Thr Asp Lys Ala Asp Leu
                195                 200                 205

Arg Leu Ile Tyr Leu Ala Leu Ala His Met Ile Lys Phe Arg Gly His
210                 215                 220

Phe Leu Ile Glu Gly Asp Leu Asn Pro Asp Asn Ser Asp Val Asp Lys
225                 230                 235                 240

Leu Phe Ile Gln Leu Val Gln Thr Tyr Asn Gln Leu Phe Glu Glu Asn
                245                 250                 255

Pro Ile Asn Ala Ser Gly Val Asp Ala Lys Ala Ile Leu Ser Ala Arg
                260                 265                 270

Leu Ser Lys Ser Arg Arg Leu Glu Asn Leu Ile Ala Gln Leu Pro Gly
                275                 280                 285

Glu Lys Lys Asn Gly Leu Phe Gly Asn Leu Ile Ala Leu Ser Leu Gly
                290                 295                 300

Leu Thr Pro Asn Phe Lys Ser Asn Phe Asp Leu Ala Glu Asp Ala Lys
305                 310                 315                 320

Leu Gln Leu Ser Lys Asp Thr Tyr Asp Asp Asp Leu Asp Asn Leu Leu
                325                 330                 335

Ala Gln Ile Gly Asp Gln Tyr Ala Asp Leu Phe Leu Ala Ala Lys Asn
                340                 345                 350

Leu Ser Asp Ala Ile Leu Leu Ser Asp Ile Leu Arg Val Asn Thr Glu
                355                 360                 365

Ile Thr Lys Ala Pro Leu Ser Ala Ser Met Ile Lys Arg Tyr Asp Glu
370                 375                 380
```

```
His His Gln Asp Leu Thr Leu Leu Lys Ala Leu Val Arg Gln Gln Leu
385                 390                 395                 400

Pro Glu Lys Tyr Lys Glu Ile Phe Phe Asp Gln Ser Lys Asn Gly Tyr
                405                 410                 415

Ala Gly Tyr Ile Asp Gly Gly Ala Ser Gln Glu Glu Phe Tyr Lys Phe
            420                 425                 430

Ile Lys Pro Ile Leu Glu Lys Met Asp Gly Thr Glu Glu Leu Leu Val
        435                 440                 445

Lys Leu Asn Arg Glu Asp Leu Leu Arg Lys Gln Arg Thr Phe Asp Asn
    450                 455                 460

Gly Ser Ile Pro His Gln Ile His Leu Gly Leu His Ala Ile Leu
465                 470                 475                 480

Arg Arg Gln Glu Asp Phe Tyr Pro Phe Leu Lys Asp Asn Arg Glu Lys
                485                 490                 495

Ile Glu Lys Ile Leu Thr Phe Arg Ile Pro Tyr Tyr Val Gly Pro Leu
            500                 505                 510

Ala Arg Gly Asn Ser Arg Phe Ala Trp Met Thr Arg Lys Ser Glu Glu
        515                 520                 525

Thr Ile Thr Pro Trp Asn Phe Glu Glu Val Val Asp Lys Gly Ala Ser
    530                 535                 540

Ala Gln Ser Phe Ile Glu Arg Met Thr Asn Phe Asp Lys Asn Leu Pro
545                 550                 555                 560

Asn Glu Lys Val Leu Pro Lys His Ser Leu Leu Tyr Glu Tyr Phe Thr
                565                 570                 575

Val Tyr Asn Glu Leu Thr Lys Val Lys Tyr Val Thr Glu Gly Met Arg
            580                 585                 590

Lys Pro Ala Phe Leu Ser Gly Glu Gln Lys Lys Ala Ile Val Asp Leu
        595                 600                 605

Leu Phe Lys Thr Asn Arg Lys Val Thr Val Lys Gln Leu Lys Glu Asp
    610                 615                 620

Tyr Phe Lys Lys Ile Glu Cys Phe Asp Ser Val Glu Ile Ser Gly Val
625                 630                 635                 640

Glu Asp Arg Phe Asn Ala Ser Leu Gly Thr Tyr His Asp Leu Leu Lys
                645                 650                 655

Ile Ile Lys Asp Lys Asp Phe Leu Asp Asn Glu Glu Asn Glu Asp Ile
            660                 665                 670

Leu Glu Asp Ile Val Leu Thr Leu Thr Leu Phe Glu Asp Arg Glu Met
        675                 680                 685

Ile Glu Glu Arg Leu Lys Thr Tyr Ala His Leu Phe Asp Asp Lys Val
    690                 695                 700

Met Lys Gln Leu Lys Arg Arg Arg Tyr Thr Gly Trp Gly Arg Leu Ser
705                 710                 715                 720

Arg Lys Leu Ile Asn Gly Ile Arg Asp Lys Gln Ser Gly Lys Thr Ile
                725                 730                 735

Leu Asp Phe Leu Lys Ser Asp Gly Phe Ala Asn Arg Asn Phe Met Gln
            740                 745                 750

Leu Ile His Asp Asp Ser Leu Thr Phe Lys Glu Asp Ile Gln Lys Ala
        755                 760                 765

Gln Val Ser Gly Gln Gly Asp Ser Leu His Glu His Ile Ala Asn Leu
    770                 775                 780

Ala Gly Ser Pro Ala Ile Lys Lys Gly Ile Leu Gln Thr Val Lys Val
785                 790                 795                 800
```

```
Val Asp Glu Leu Val Lys Val Met Gly Arg His Lys Pro Glu Asn Ile
            805                 810                 815
Val Ile Glu Met Ala Arg Glu Asn Gln Thr Thr Gln Lys Gly Gln Lys
        820                 825                 830
Asn Ser Arg Glu Arg Met Lys Arg Ile Glu Glu Gly Ile Lys Glu Leu
        835                 840                 845
Gly Ser Gln Ile Leu Lys Glu His Pro Val Glu Asn Thr Gln Leu Gln
        850                 855                 860
Asn Glu Lys Leu Tyr Leu Tyr Tyr Leu Gln Asn Gly Arg Asp Met Tyr
865                 870                 875                 880
Val Asp Gln Glu Leu Asp Ile Asn Arg Leu Ser Asp Tyr Asp Val Asp
            885                 890                 895
His Ile Val Pro Gln Ser Phe Leu Lys Asp Asp Ser Ile Asp Asn Lys
            900                 905                 910
Val Leu Thr Arg Ser Asp Lys Asn Arg Gly Lys Ser Asp Asn Val Pro
            915                 920                 925
Ser Glu Glu Val Val Lys Lys Met Lys Asn Tyr Trp Arg Gln Leu Leu
            930                 935                 940
Asn Ala Lys Leu Ile Thr Gln Arg Lys Phe Asp Asn Leu Thr Lys Ala
945                 950                 955                 960
Glu Arg Gly Gly Leu Ser Glu Leu Asp Lys Ala Gly Phe Ile Lys Arg
                965                 970                 975
Gln Leu Val Glu Thr Arg Gln Ile Thr Lys His Val Ala Gln Ile Leu
            980                 985                 990
Asp Ser Arg Met Asn Thr Lys Tyr Asp Glu Asn Asp Lys Leu Ile Arg
            995                 1000                1005
Glu Val Lys Val Ile Thr Leu Lys Ser Lys Leu Val Ser Asp Phe
        1010                1015                1020
Arg Lys Asp Phe Gln Phe Tyr Lys Val Arg Glu Ile Asn Asn Tyr
        1025                1030                1035
His His Ala His Asp Ala Tyr Leu Asn Ala Val Val Gly Thr Ala
        1040                1045                1050
Leu Ile Lys Lys Tyr Pro Lys Leu Glu Ser Glu Phe Val Tyr Gly
        1055                1060                1065
Asp Tyr Lys Val Tyr Asp Val Arg Lys Met Ile Ala Lys Ser Glu
        1070                1075                1080
Gln Glu Ile Gly Lys Ala Thr Ala Lys Tyr Phe Phe Tyr Ser Asn
        1085                1090                1095
Ile Met Asn Phe Phe Lys Thr Glu Ile Thr Leu Ala Asn Gly Glu
        1100                1105                1110
Ile Arg Lys Arg Pro Leu Ile Glu Thr Asn Gly Glu Thr Gly Glu
        1115                1120                1125
Ile Val Trp Asp Lys Gly Arg Asp Phe Ala Thr Val Arg Lys Val
        1130                1135                1140
Leu Ser Met Pro Gln Val Asn Ile Val Lys Lys Thr Glu Val Gln
        1145                1150                1155
Thr Gly Gly Phe Ser Lys Glu Ser Ile Leu Pro Lys Arg Asn Ser
        1160                1165                1170
Asp Lys Leu Ile Ala Arg Lys Lys Asp Trp Asp Pro Lys Lys Tyr
        1175                1180                1185
Gly Gly Phe Asp Ser Pro Thr Val Ala Tyr Ser Val Leu Val Val
        1190                1195                1200
Ala Lys Val Glu Lys Gly Lys Ser Lys Lys Leu Lys Ser Val Lys
```

```
                1205                1210                1215

Glu Leu Leu Gly Ile Thr Ile Met Glu Arg Ser Ser Phe Glu Lys
            1220                1225                1230

Asn Pro Ile Asp Phe Leu Glu Ala Lys Gly Tyr Lys Glu Val Lys
            1235                1240                1245

Lys Asp Leu Ile Ile Lys Leu Pro Lys Tyr Ser Leu Phe Glu Leu
            1250                1255                1260

Glu Asn Gly Arg Lys Arg Met Leu Ala Ser Ala Gly Glu Leu Gln
            1265                1270                1275

Lys Gly Asn Glu Leu Ala Leu Pro Ser Lys Tyr Val Asn Phe Leu
            1280                1285                1290

Tyr Leu Ala Ser His Tyr Glu Lys Leu Lys Gly Ser Pro Glu Asp
            1295                1300                1305

Asn Glu Gln Lys Gln Leu Phe Val Glu Gln His Lys His Tyr Leu
            1310                1315                1320

Asp Glu Ile Ile Glu Gln Ile Ser Glu Phe Ser Lys Arg Val Ile
            1325                1330                1335

Leu Ala Asp Ala Asn Leu Asp Lys Val Leu Ser Ala Tyr Asn Lys
            1340                1345                1350

His Arg Asp Lys Pro Ile Arg Glu Gln Ala Glu Asn Ile Ile His
            1355                1360                1365

Leu Phe Thr Leu Thr Asn Leu Gly Ala Pro Ala Ala Phe Lys Tyr
            1370                1375                1380

Phe Asp Thr Thr Ile Asp Arg Lys Arg Tyr Thr Ser Thr Lys Glu
            1385                1390                1395

Val Leu Asp Ala Thr Leu Ile His Gln Ser Ile Thr Gly Leu Tyr
            1400                1405                1410

Glu Thr Arg Ile Asp Leu Ser Gln Leu Gly Gly Asp Lys Arg Pro
            1415                1420                1425

Ala Ala Thr Lys Lys Ala Gly Gln Ala Lys Lys Lys Lys Gly Ser
            1430                1435                1440

Gly Ser Asn Gly Ser Ser Gly Ser Ala Ser Lys Gly Glu Arg Leu
            1445                1450                1455

Phe Arg Gly Lys Val Pro Ile Leu Val Glu Leu Lys Gly Asp Val
            1460                1465                1470

Asn Gly His Lys Phe Ser Val Arg Gly Lys Gly Lys Gly Asp Ala
            1475                1480                1485

Thr Arg Gly Lys Leu Thr Leu Lys Phe Ile Cys Thr Thr Gly Lys
            1490                1495                1500

Leu Pro Val Pro Trp Pro Thr Leu Val Thr Thr Leu Thr Tyr Gly
            1505                1510                1515

Val Gln Cys Phe Ser Arg Tyr Pro Lys His Met Lys Arg His Asp
            1520                1525                1530

Phe Phe Lys Ser Ala Met Pro Lys Gly Tyr Val Gln Glu Arg Thr
            1535                1540                1545

Ile Ser Phe Lys Lys Asp Gly Lys Tyr Lys Thr Arg Ala Glu Val
            1550                1555                1560

Lys Phe Glu Gly Arg Thr Leu Val Asn Arg Ile Lys Leu Lys Gly
            1565                1570                1575

Arg Asp Phe Lys Glu Lys Gly Asn Ile Leu Gly His Lys Leu Arg
            1580                1585                1590

Tyr Asn Phe Asn Ser His Lys Val Tyr Ile Thr Ala Asp Lys Arg
            1595                1600                1605
```

```
Lys Asn Gly Ile Lys Ala Lys Phe Lys Ile Arg His Asn Val Lys
    1610            1615                1620

Asp Gly Ser Val Gln Leu Ala Asp His Tyr Gln Gln Asn Thr Pro
    1625            1630                1635

Ile Gly Arg Gly Pro Val Leu Leu Pro Arg Asn His Tyr Leu Ser
    1640            1645                1650

Thr Arg Ser Lys Leu Ser Lys Asp Pro Lys Glu Lys Arg Asp His
    1655            1660                1665

Met Val Leu Leu Glu Phe Val Thr Ala Ala Gly Ile Lys His Gly
    1670            1675                1680

Arg Asp Glu Arg Tyr Lys Gly Gly Ser Gly Gly Ser Val Asp Gly
    1685            1690                1695

Leu Phe Glu Ala Ile Glu Gly Phe Ile Glu Asn Gly Trp Glu Gly
    1700            1705                1710

Met Ile Asp Gly Trp Tyr Gly
    1715            1720

<210> SEQ ID NO 5
<211> LENGTH: 26
<212> TYPE: DNA
<213> ORGANISM: Artificial sequence
<220> FEATURE:
<223> OTHER INFORMATION: Synthetic construct

<400> SEQUENCE: 5
gctaattcac tcccaaagaa gacaag                                    26

<210> SEQ ID NO 6
<211> LENGTH: 20
<212> TYPE: DNA
<213> ORGANISM: Artificial sequence
<220> FEATURE:
<223> OTHER INFORMATION: Synthetic construct

<400> SEQUENCE: 6
cttcagcaag ccgagtcctg                                           20

<210> SEQ ID NO 7
<211> LENGTH: 60
<212> TYPE: DNA
<213> ORGANISM: Artificial sequence
<220> FEATURE:
<223> OTHER INFORMATION: Synthetic construct

<400> SEQUENCE: 7
gtcgacgtcg acgctcagtg aagctgaagt attccttctg cttcacaggg cgaccactac   60

<210> SEQ ID NO 8
<211> LENGTH: 49
<212> TYPE: DNA
<213> ORGANISM: Artificial sequence
<220> FEATURE:
<223> OTHER INFORMATION: Synthetic construct

<400> SEQUENCE: 8
atttaaatcc tccctcgaa cccttaccaa actcctatgc atactacag             49

<210> SEQ ID NO 9
<211> LENGTH: 60
<212> TYPE: DNA
<213> ORGANISM: Artificial sequence
<220> FEATURE:
```

<223> OTHER INFORMATION: Synthetic construct

<400> SEQUENCE: 9
ttaattaatt aattagcatt ttaggttcag gttgtgagaa cactagaaga gaacaagtca    60

<210> SEQ ID NO 10
<211> LENGTH: 52
<212> TYPE: DNA
<213> ORGANISM: Artificial sequence
<220> FEATURE:
<223> OTHER INFORMATION: Synthetic construct

<400> SEQUENCE: 10
gtatacgtat acgcatacct ggagagggga caaggtcttg agatgcgagg gt    52

<210> SEQ ID NO 11
<211> LENGTH: 52
<212> TYPE: DNA
<213> ORGANISM: Artificial sequence
<220> FEATURE:
<223> OTHER INFORMATION: Synthetic construct

<400> SEQUENCE: 11
agccacctta attaagccac catggcgcac gctgggagaa cggggtacga ta    52

<210> SEQ ID NO 12
<211> LENGTH: 60
<212> TYPE: DNA
<213> ORGANISM: Artificial sequence
<220> FEATURE:
<223> OTHER INFORMATION: Synthetic construct

<400> SEQUENCE: 12
taacagagag aagttcgtgg ctccggatcc cttgtggccc agataggcac ccagggtgat    60

<210> SEQ ID NO 13
<211> LENGTH: 24
<212> TYPE: DNA
<213> ORGANISM: Artificial sequence
<220> FEATURE:
<223> OTHER INFORMATION: Synthetic construct

<400> SEQUENCE: 13
caccgtgaga tacagataca gaca    24

<210> SEQ ID NO 14
<211> LENGTH: 24
<212> TYPE: DNA
<213> ORGANISM: ARtificial sequence
<220> FEATURE:
<223> OTHER INFORMATION: Synthetic construct

<400> SEQUENCE: 14
aaactgtctg tatctgtatc tcac    24

<210> SEQ ID NO 15
<211> LENGTH: 25
<212> TYPE: DNA
<213> ORGANISM: Artificial sequence
<220> FEATURE:
<223> OTHER INFORMATION: Synthetic construct

<400> SEQUENCE: 15
aaacggcatt ccaggcaaat cattc    25

```
<210> SEQ ID NO 16
<211> LENGTH: 25
<212> TYPE: DNA
<213> ORGANISM: Artificial sequence
<220> FEATURE:
<223> OTHER INFORMATION: Synthetic construct

<400> SEQUENCE: 16
caccgcagcc taggcaaagg cctgc                                        25

<210> SEQ ID NO 17
<211> LENGTH: 25
<212> TYPE: DNA
<213> ORGANISM: Artificial sequence
<220> FEATURE:
<223> OTHER INFORMATION: Synthetic construct

<400> SEQUENCE: 17
aaacgcaggc ctttgcctag gctgc                                        25

<210> SEQ ID NO 18
<211> LENGTH: 25
<212> TYPE: DNA
<213> ORGANISM: Artificial sequence
<220> FEATURE:
<223> OTHER INFORMATION: Synthetic construct

<400> SEQUENCE: 18
caccgtgcca acagaactgc ctgat                                        25

<210> SEQ ID NO 19
<211> LENGTH: 25
<212> TYPE: DNA
<213> ORGANISM: Artificial sequence
<220> FEATURE:
<223> OTHER INFORMATION: Synthetic construct

<400> SEQUENCE: 19
aaacatcagg cagttctgtt ggcac                                        25

<210> SEQ ID NO 20
<211> LENGTH: 24
<212> TYPE: DNA
<213> ORGANISM: Artificial sequence
<220> FEATURE:
<223> OTHER INFORMATION: Synthetic construct

<400> SEQUENCE: 20
caccgaccag ggtgcaagtg tgga                                         24

<210> SEQ ID NO 21
<211> LENGTH: 24
<212> TYPE: DNA
<213> ORGANISM: Artificial sequence
<220> FEATURE:
<223> OTHER INFORMATION: Synthetic construct

<400> SEQUENCE: 21
aaactccaca cttgcaccct ggtc                                         24

<210> SEQ ID NO 22
<211> LENGTH: 24
<212> TYPE: DNA
<213> ORGANISM: Artificial sequence
<220> FEATURE:
<223> OTHER INFORMATION: Synthetic construct
```

```
<400> SEQUENCE: 22
caccgctcct cagcctggca ttca                                              24

<210> SEQ ID NO 23
<211> LENGTH: 24
<212> TYPE: DNA
<213> ORGANISM: Artificial sequence
<220> FEATURE:
<223> OTHER INFORMATION: Synthetic construct

<400> SEQUENCE: 23
aaactgaatg ccaggctgag gagc                                              24

<210> SEQ ID NO 24
<211> LENGTH: 23
<212> TYPE: DNA
<213> ORGANISM: Artificial sequence
<220> FEATURE:
<223> OTHER INFORMATION: Synthetic construct

<400> SEQUENCE: 24
tgctaaagcg catgctccag act                                               23

<210> SEQ ID NO 25
<211> LENGTH: 21
<212> TYPE: DNA
<213> ORGANISM: Artificial sequence
<220> FEATURE:
<223> OTHER INFORMATION: Synthetic construct

<400> SEQUENCE: 25
gtcttcatct cagggtcggc t                                                 21

<210> SEQ ID NO 26
<211> LENGTH: 21
<212> TYPE: DNA
<213> ORGANISM: Artificial sequence
<220> FEATURE:
<223> OTHER INFORMATION: Synthetic construct

<400> SEQUENCE: 26
cctctctgtg cattatggca g                                                 21

<210> SEQ ID NO 27
<211> LENGTH: 19
<212> TYPE: DNA
<213> ORGANISM: Artificial sequence
<220> FEATURE:
<223> OTHER INFORMATION: Synthetic construct

<400> SEQUENCE: 27
gccttctatc gccttcttg                                                    19

<210> SEQ ID NO 28
<211> LENGTH: 20
<212> TYPE: DNA
<213> ORGANISM: Artificial sequence
<220> FEATURE:
<223> OTHER INFORMATION: Synthetic construct

<400> SEQUENCE: 28
actcctccac ctttgacgct                                                   20

<210> SEQ ID NO 29
<211> LENGTH: 23
```

```
<212> TYPE: DNA
<213> ORGANISM: Artificial sequence
<220> FEATURE:
<223> OTHER INFORMATION: Synthetic construct

<400> SEQUENCE: 29
tcccctcttc aagggtctac atg                                             23

<210> SEQ ID NO 30
<211> LENGTH: 20
<212> TYPE: DNA
<213> ORGANISM: Artificial sequence
<220> FEATURE:
<223> OTHER INFORMATION: Synthetic construct

<400> SEQUENCE: 30
gtgcaaaatg gaagggtttc                                                 20

<210> SEQ ID NO 31
<211> LENGTH: 20
<212> TYPE: DNA
<213> ORGANISM: Artificial sequence
<220> FEATURE:
<223> OTHER INFORMATION: Synthetic construct

<400> SEQUENCE: 31
ggagctccgt gaagttgttc                                                 20

<210> SEQ ID NO 32
<211> LENGTH: 21
<212> TYPE: DNA
<213> ORGANISM: Artificial sequence
<220> FEATURE:
<223> OTHER INFORMATION: Synthetic construct

<400> SEQUENCE: 32
tgtttccttt cactggccac a                                               21

<210> SEQ ID NO 33
<211> LENGTH: 21
<212> TYPE: DNA
<213> ORGANISM: Artificial sequence
<220> FEATURE:
<223> OTHER INFORMATION: Synthetic construct

<400> SEQUENCE: 33
aacggcaact ggtgaacggt a                                               21

<210> SEQ ID NO 34
<211> LENGTH: 22
<212> TYPE: DNA
<213> ORGANISM: Artificial sequence
<220> FEATURE:
<223> OTHER INFORMATION: Synthetic construct

<400> SEQUENCE: 34
ggcgatgcca gaatagatgc cg                                              22

<210> SEQ ID NO 35
<211> LENGTH: 29
<212> TYPE: DNA
<213> ORGANISM: Artificial sequence
<220> FEATURE:
<223> OTHER INFORMATION: Synthetic construct

<400> SEQUENCE: 35
```
ccaggccact tggctcctct atctccaga                                    29

<210> SEQ ID NO 36
<211> LENGTH: 25
<212> TYPE: DNA
<213> ORGANISM: Artificial sequence
<220> FEATURE:
<223> OTHER INFORMATION: Synthetic construct

<400> SEQUENCE: 36
ccttactgtt gagactgcaa tatcc                                        25

<210> SEQ ID NO 37
<211> LENGTH: 26
<212> TYPE: DNA
<213> ORGANISM: Artificial sequence
<220> FEATURE:
<223> OTHER INFORMATION: Synthetic construct

<400> SEQUENCE: 37
ctgaagtccc agtatatact tcacac                                       26

<210> SEQ ID NO 38
<211> LENGTH: 25
<212> TYPE: DNA
<213> ORGANISM: Artificial sequence
<220> FEATURE:
<223> OTHER INFORMATION: Synthetic construct

<400> SEQUENCE: 38
cccagaagca gtaataatca tcgag                                        25

<210> SEQ ID NO 39
<211> LENGTH: 23
<212> TYPE: DNA
<213> ORGANISM: Artificial sequence
<220> FEATURE:
<223> OTHER INFORMATION: Synthetic construct

<400> SEQUENCE: 39
atgtgggatg tagtagatct tgc                                          23

<210> SEQ ID NO 40
<211> LENGTH: 21
<212> TYPE: DNA
<213> ORGANISM: Artificial sequence
<220> FEATURE:
<223> OTHER INFORMATION: Synthetic construct

<400> SEQUENCE: 40
gggtcttacc tcagcagtta c                                            21

<210> SEQ ID NO 41
<211> LENGTH: 20
<212> TYPE: DNA
<213> ORGANISM: Artificial sequence
<220> FEATURE:
<223> OTHER INFORMATION: synthetic construct

<400> SEQUENCE: 41
cctcacacag tgtgacgcag                                              20

<210> SEQ ID NO 42
<211> LENGTH: 20
<212> TYPE: DNA
<213> ORGANISM: Artificial sequence

```
<220> FEATURE:
<223> OTHER INFORMATION: Synthetic construct

<400> SEQUENCE: 42
gactgagtac ctgaaccggc                                                     20

<210> SEQ ID NO 43
<211> LENGTH: 20
<212> TYPE: DNA
<213> ORGANISM: Artificial sequence
<220> FEATURE:
<223> OTHER INFORMATION: Synthetic construct

<400> SEQUENCE: 43
gggccaaact gagcagagtc                                                     20

<210> SEQ ID NO 44
<211> LENGTH: 20
<212> TYPE: DNA
<213> ORGANISM: Artificial sequence
<220> FEATURE:
<223> OTHER INFORMATION: Synthetic construct

<400> SEQUENCE: 44
aagaccaggg tggttgggac                                                     20

<210> SEQ ID NO 45
<211> LENGTH: 20
<212> TYPE: DNA
<213> ORGANISM: Artificial sequence
<220> FEATURE:
<223> OTHER INFORMATION: Synthetic construct

<400> SEQUENCE: 45
gtaagaaaaa tgcccacgtc                                                     20

<210> SEQ ID NO 46
<211> LENGTH: 20
<212> TYPE: DNA
<213> ORGANISM: Artificial sequence
<220> FEATURE:
<223> OTHER INFORMATION: Synthetic construct

<400> SEQUENCE: 46
agtcagacgt ctggagcttc                                                     20

<210> SEQ ID NO 47
<211> LENGTH: 22
<212> TYPE: DNA
<213> ORGANISM: Artificial sequence
<220> FEATURE:
<223> OTHER INFORMATION: Synthetic construct

<400> SEQUENCE: 47
gtgagcagtg aaggcatgag tc                                                  22

<210> SEQ ID NO 48
<211> LENGTH: 20
<212> TYPE: DNA
<213> ORGANISM: Artificial sequence
<220> FEATURE:
<223> OTHER INFORMATION: Synthetic construct

<400> SEQUENCE: 48
gtgagataca gatacagaca                                                     20
```

```
<210> SEQ ID NO 49
<211> LENGTH: 20
<212> TYPE: DNA
<213> ORGANISM: Artificial sequence
<220> FEATURE:
<223> OTHER INFORMATION: Synthetic construct

<400> SEQUENCE: 49
aatgatttgc ctggaatgcc                                              20

<210> SEQ ID NO 50
<211> LENGTH: 23
<212> TYPE: PRT
<213> ORGANISM: Artificial sequence
<220> FEATURE:
<223> OTHER INFORMATION: Synthetic construct

<400> SEQUENCE: 50

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 51
<211> LENGTH: 14
<212> TYPE: PRT
<213> ORGANISM: Artificial sequence
<220> FEATURE:
<223> OTHER INFORMATION: Synthetic construct

<400> SEQUENCE: 51

Tyr Gly Arg Lys Lys Arg Arg Gln Arg Arg Pro Pro Gln
1               5                   10

<210> SEQ ID NO 52
<211> LENGTH: 91
<212> TYPE: DNA
<213> ORGANISM: Artificial sequence
<220> FEATURE:
<223> OTHER INFORMATION: Synthetic construct

<400> SEQUENCE: 52
atccacgttc accttgcccc acagggcagt aacggcagac ttctcctcag gagtcaggtg   60
caccatggtg tctgtttgag gttgctagtg a                                 91

<210> SEQ ID NO 53
<211> LENGTH: 95
<212> TYPE: DNA
<213> ORGANISM: Artificial sequence
<220> FEATURE:
<223> OTHER INFORMATION: Synthetic construct

<400> SEQUENCE: 53
cttcatccac gttcaccttg ccccacaggg cagtaacggc agattttttcc tcaggagtca   60 ggtgcaccat ggtgtctgtt tgaggttgct agtga                             95

<210> SEQ ID NO 54
<211> LENGTH: 39
<212> TYPE: DNA
<213> ORGANISM: Artificial sequence
<220> FEATURE:
<223> OTHER INFORMATION: Synthetic construct

<400> SEQUENCE: 54
```

```
taatacgact cactataggg taacggcaga cttctccac                           39

<210> SEQ ID NO 55
<211> LENGTH: 21
<212> TYPE: DNA
<213> ORGANISM: Artificial sequence
<220> FEATURE:
<223> OTHER INFORMATION: Synthetic construct

<400> SEQUENCE: 55
aaaaagcacc gactcggtgc c                                             21

<210> SEQ ID NO 56
<211> LENGTH: 14
<212> TYPE: DNA
<213> ORGANISM: Artificial sequence
<220> FEATURE:
<223> OTHER INFORMATION: Synthetic construct

<400> SEQUENCE: 56
tcctgaggaa aaat                                                     14

<210> SEQ ID NO 57
<211> LENGTH: 16
<212> TYPE: DNA
<213> ORGANISM: Artificial sequence
<220> FEATURE:
<223> OTHER INFORMATION: Synthetic construct

<400> SEQUENCE: 57
tgactcctga ggagaa                                                   16

<210> SEQ ID NO 58
<211> LENGTH: 15
<212> TYPE: DNA
<213> ORGANISM: Artificial sequence
<220> FEATURE:
<223> OTHER INFORMATION: Synthetic construct

<400> SEQUENCE: 58
actcctgtgg agaag                                                    15

<210> SEQ ID NO 59
<211> LENGTH: 25
<212> TYPE: DNA
<213> ORGANISM: Artificial sequence
<220> FEATURE:
<223> OTHER INFORMATION: Synthetic construct

<400> SEQUENCE: 59
cagagccatc tattgcttac atttg                                         25

<210> SEQ ID NO 60
<211> LENGTH: 20
<212> TYPE: DNA
<213> ORGANISM: Artificial sequence
<220> FEATURE:
<223> OTHER INFORMATION: Synthetic construct

<400> SEQUENCE: 60
ggcctcacca ccaacttcat                                               20
```

US 11,555,207 B2

CRISPR/CAS9 COMPLEX FOR INTRODUCING A FUNCTIONAL POLYPEPTIDE INTO CELLS OF BLOOD CELL LINEAGE

This application claims the benefit of U.S. Provisional Application No. 62/181,145, filed Jun. 17, 2015, which is hereby incorporated in its entirety by this reference.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 1071089_SeqList.txt, created on Jun. 13, 2018, and having a size of 44 KB. The sequence listing contained in this ASCII formatted document is part of the specification and is herein incorporated by reference in its entirety.

BACKGROUND

Clustered regularly interspaced short palindromic repeats (CRISPR)-associated (Cas) systems (CRISPR-Cas9 systems) are used for gene editing at desired genomic sites in mammalian cells. In CRISPR-Cas9 systems, a Cas9 nuclease is targeted to a genomic site by complexing with a guide RNA that hybridizes to a target site in the genome. This results in a double-strand break that initiates either non-homologous end-joining (NHEJ) or homology-directed repair (HDR) of genomic DNA via a double-strand or single-strand DNA repair template. However, repair of a genomic site via HDR is inefficient.

SUMMARY

Provided herein are complexes and methods for introducing a functional polypeptide into cells of blood lineage. Provided herein is a method of making tumor-specific T-cell precursor cells the method comprises introducing into a population of T-cell precursor cells a complex comprising: (a) a guide (gRNA) comprising a first nucleotide sequence that hybridizes to a target DNA in the genome of the T cell precursor cells and a second nucleotide sequence that interacts with a site-directed nuclease; (b) a recombinant site-directed nuclease operably linked to a supercharged protein, wherein the site-directed nuclease comprises an RNA-binding portion that interacts with the second nucleotide sequence of the gRNA and wherein the site-directed nuclease specifically binds and cleaves the target DNA to create a double stranded break; and (c) a donor nucleic sequence comprising a third nucleotide sequence that encodes a chimeric antigen receptor (CAR) and a fourth nucleotide sequence that hybridizes to a genomic sequence flanking the double stranded break in the target DNA, wherein the complex is introduced into the T-cell precursor cells under conditions that allow homology-directed repair (HDR) and integration of the third nucleotide sequence into the target DNA to form modified T-cell precursor cells that express the CAR. The method further provides for a high rate of cell survival in the modified T-cell precursor cells. Also provided are complexes for making tumor-specific T-cell precursor cells.

DESCRIPTION OF THE FIGURES

FIGS. 1A and 1B show flow cytometry of iPSC-derived T cells. JAK3 WT iPSCs (Control) and JAK3- deficient iPSCs (JAK3 C1837T) were differentiated into CD34+ cells on OP9 stromal cells and, subsequently, into T cells on OP9-DL4 monolayers. T-cell differentiation from JAK3-deficient iPSCs was absent compared to controls; no CD3+ T cells or CD3-CD16+CD56+ NK cells were observed (FIG. 1A), and no CD4+CD8+ double positive (DP), CD4+ single positive (SP), or CD8+ single positive (SP) T cells were detected (FIG. 1B). FIG. 1C shows the results of RT-qPCR assays for transcripts of key genes that regulate early events during specification of the T cell lineage. RNA levels are shown relative to GAPDH expression.

FIG. 2A shows apoptosis of JAK3-deficient, iPSC-derived T cells compared to JAK3 WT controls. Annexin V-positive cells were analyzed at T cell induction day 10 (TD10) and 17 (TD17). Four independent experiments were performed with control JAK3 WT cells (Control) and 5 independent experiments were performed with JAK3-deficient cells (JAK3 C1837 T). *$P$ <0.005. FIG. 2B shows the results of RT-qPCR assays for anti-apoptotic BCL2 and proapoptotic BAX expression in two lines (1 and 2) from JAK3 WT (Control) and JAK3-deficient cells (JAK3 C1837T). ND, not determined (due to insignificant JAK3 qPCR signal). RNA levels are shown relative to GAPDH expression. FIG. 2C shows flow cytometry of JAK3-deficient iPSCderived T cells transduced with BCL2-2 A-GFP lentivirus to assess effects on NK (CD16+56+) and T cell (CD3+) development and DP (CD4+CD8+) to SP (CD4+or CD8+) T cell maturation.

FIG. 3A depicts the strategy for genome modification using CRISPR/Cas9 to induce double-strand breaks in the JAK3 locus and a template for homology directed repair. Top line, structure of the JAK3 gene. Open boxes, exons. Asterisk, C1837 T mutation. Arrows, guide RNAs. FIG. 3B, top, shows PCR analysis demonstrating homologous recombination; primers for 5' and 3' analysis are indicated. (Lower Left) RT-PCR analysis demonstrating JAK3 mRNA expression in JAK3 WT (Control), JAK3-deficient (JAK3 C1837 T), and corrected (JAK3 Corrected) T cells. (Lower Right) Western Blot analysis demonstrating JAK3 protein expression in JAK3 WT (Control), JAK3-deficient (JAK3 C1837 T), and corrected (JAK3 Corrected) T cells. FIG. 3C provides a summary of targeting efficiencies of guide RNAs. (FIG. 3D) Sanger sequencing of the PCR amplicons from parental JAK3 iPSCs (Left), heterozygous corrected (Middle) and homozygous corrected iPSCs (Right). The two heterozygous clones were corrected with gRNA2+wild type Cas9, and the homozygous clone was corrected with gRNA1+gRNA2+nickase Cas9 (D10A).

FIG. 4A shows the expression of T cell developmental markers in JAK3 WT (Control, n=3), JAK3-deficient (JAK3 C1837 T, n=5) and JAK3-corrected (JAK3 Corrected, n=6) T cells. Cells were stained with indicated antibodies and analyzed by flow cytometry at T cell induction Day 14, 21, 28 and 35 (TD 14, 21, 28 and 35). FIG. 4B shows T cell receptor (TCR) Vβ analysis of JAK3-corrected T cells. A highly diverse repertoire of TCR Vβ is represented in T cells derived from corrected SCID patient iPSCs. FIG. 4C shows flow cytometry demonstrating T cell activation in JAK3-corrected T cells. T cells derived from JAK3 WT (Control) and JAK3-corrected iPSCs were stimulated with anti-CD3/28 beads for 3 days before analysis of activation markers CD25 and CD69. The data were gated on CD3+ populations.

DETAILED DESCRIPTION

Figure 1A:
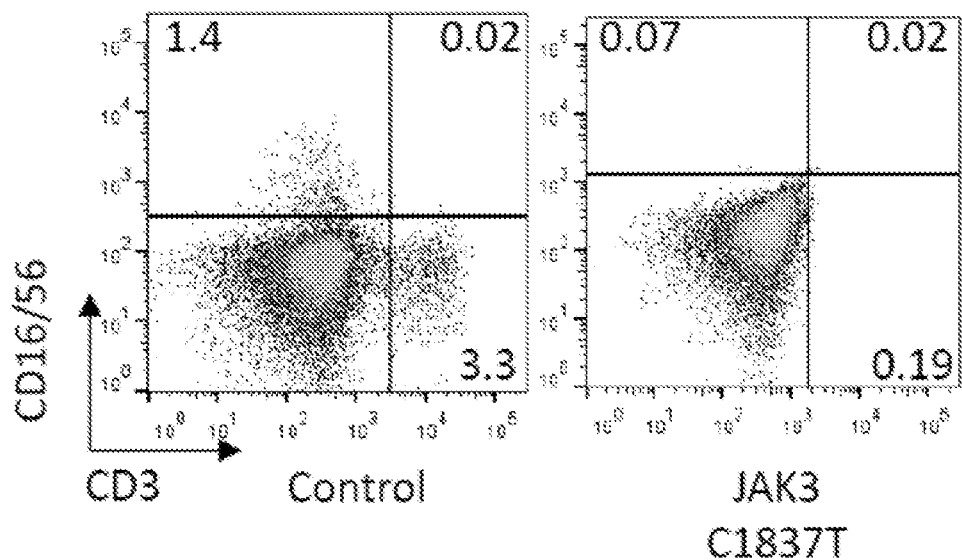
FIGS. 1A-1C show that in vitro differentiation of JAK3 C1837 T patient iPSCs recapitulates SCID phenotypes.

Provided herein are CRISPR/Cas9 complexes for genomic modification of cells. Methods of using the complexes provided herein result in increased efficiency of modification, an increased cell survival ratio and/or an increased ratio of HDR to NHEJ in the cells. These complexes and methods can be used for therapeutic purposes, for example, to correct a mutation in cells, wherein the mutation is associated with a disease or disorder.

Provided herein is a complex for correcting a mutation in the genome of a cell comprising (a) a guide RNA (gRNA) comprising a first nucleotide sequence that hybridizes to a target DNA in the genome of a cell, wherein the target DNA comprises a mutation, and a second nucleotide sequence that interacts with a site-directed nuclease; (b) a recombinant site-directed nuclease operably linked to a supercharged protein, wherein the site-directed nuclease comprises an RNA-binding portion that interacts with the second nucleotide sequence of the guide RNA and wherein the site-directed nuclease specifically binds and cleaves the target DNA to create a double stranded break; and (c) a single-stranded donor oligonucleotide (ssODN) that hybridizes to a genomic sequence flanking the double stranded break in the target DNA and integrates into the target DNA to correct a mutation in the target DNA. It is understood that the complex comprising a guide RNA (gRNA), a recombinant site-directed nuclease and a donor nucleotide described herein does not occur in nature. The complex, however, provides the elements necessary with the required configuration and stoichiometry to efficiently and effectively modify cells. The gRNA molecule binds to the site-directed nuclease and targets the nuclease to a specific location within the target DNA. A gRNA comprises a first nucleotide sequence that hybridizes to a target DNA in the genome of a cell, wherein the target DNA comprises a mutation, and a second nucleotide sequence that interacts with a site-directed nuclease. The complexes described herein can comprise one or two separate gRNAs. Therefore, the term guide RNA includes both a single guide RNA and a double guide RNA. An example of a guide sequence that can be used to correct a mutation associated with sickle cell anemia is set forth herein as TAACGGCAGACTTCTCCAC (SEQ ID NO: 1). An example of a guide sequence comprising a stem loop for Cas9 binding is provided herein as GTAACGGCAGACTTCTCCACGTTTTAGAGCTAGAAATAGCAAGTTAAAATAAGG CTAGTCCGTTATCAACTTGAAAAAGTGGCACCGAGTCGGTGCTTTTTT (SEQ ID NO: 2). It is noted that the 5'G of SEQ ID NO: 2 was added by T7 during in vitro transcription.

In the complexes described herein, the recombinant site-directed nuclease can be an RNA-guided site-directed nuclease, for example, a Cas protein from any bacterial species or a functional fragment thereof. For example, the Cas protein can be a Cas9 protein or a functional fragment thereof. As used herein, the term "Cas9" means a Cas9 protein or a fragment thereof present in any bacterial species that encodes a Type II CRISPR/Cas9 system. See, for example, Makarova et al. *Nature Reviews*, Microbiology, 9:467-477 (2011), including supplemental information, hereby incorporated by reference in its entirety. For example, the Cas9 protein or a fragment thereof can be from *Streptococcus*

*pyogenes*. Full-length Cas9 is an endonuclease that includes a recognition domain and two nuclease domains (HNH and RuvC, respectively). In the amino acid sequence, HNH is linearly continuous, whereas RuvC is separated into three regions, one left of the recognition domain, and the other two right of the recognition domain flanking the HNH domain. Cas9 from *Streptococcus pyogenes* is targeted to a genomic site in a cell by interacting with a guide RNA that hybridizes to a 20-nucleotide DNA sequence that immediately precedes an NGG motif recognized by Cas9. This results in a double-strand break that is repaired via HDR by a donor nucleotide, for example, a ssODN or a double stranded DNA construct that hybridizes to a genomic sequence flanking the double stranded break in the target DNA and integrates into the target DNA to correct a mutation in the target DNA.

In the complexes provided herein, the molar ratio of gRNA to site-directed nuclease operably linked to a supercharged protein to ssODN can be from about 1:1:0.2 to about 1.5:1:2.0. For example, the molar ratio of gRNA to site-directed nuclease operably linked to a supercharged protein to ssODN can be about 1:1:1, 1.1:1:1, 1:1:1.15, 1:1:1.25, 1:1:1.30; 1:1:1.35; 1:1:1.40; 1:1:1.50, 1.2:1:1, 1.3:1:1. 1.4:1:1, 1.5:1:1, 1.5:1:1.15, 1.5:1:1.25, 1.5:1:1.35; 1.5:1:1.40, 1.5:1:1.45; 1.5:1:1.50; 1.5:1:1.55; 1.5:1:1.60; 1.5:1:1.65; 1.5:1:1.70; 1.5:1:1.75; 1.5:1:1.80; 1.5:1:1.85; 1.5:1:1.90; 1.5:1:1.95; 1.5:1: 2.0 or any ratio in between these ratios. Complexes having these molar ratios can be used in any of the methods described herein. Methods for preparing a complex prior to introducing the complex into a cell or a population of cells are set forth in the Examples.

As used herein, a supercharged protein can be a superpositively charged protein that has an overall positive charge that is greater than its corresponding unmodified protein. For example, the superpositively charged protein can be a superpositively charged green fluorescent protein (GFP) that has an overall positive charge from about +5 to about +40. For example, the overall positive charge can be about +5, +6, +7, +8, +9, +10, +11, +12, +13, +14, +15, +16, +17, +18, +19, +20, +21, +22, +23, +24, +25, +26, +27, +28, +29, +30, +31, +32, +33, +34, +35, +36, +37, +38, +39 or +40.

The supercharged protein can be operably linked to the amino-terminus or the carboxy-terminus of the nuclease. It is also contemplated that the supercharged protein can be associated with the nuclease, without necessarily being covalently linked to the nuclease. An example of a supercharged protein is a superpositively charged GFP, for example, +36 GFP. +36 GFP can be operably linked to the amino or carboxy- terminus of Cas9 or a functional fragment thereof. See, for example, McNaughton et al., "Mammalian cell penetration, siRNA transfection, and DNA transfection by supercharged proteins," *PNAS* 106 (15): 6111-6116. An example of a polypeptide comprising +36 GFP operably linked to the carboxy-terminus of Cas9 is provided herein as SEQ ID NO: 3.

The nuclease can also be operably linked to a supercharged protein and one or more positively charged peptides, for example, one or more transactivating transcriptional activator (TAT) peptide can be linked to the amino-terminus or the carboxy terminus of the nuclease. For example, and not to be limiting, a superpositively charged protein can be operably linked to the carboxy-terminus of the nuclease and one or more TAT peptides (for example, 1× TAT, 2× TAT, 3× TAT, 4× TAT, etc.) can be operably linked to the amino-terminus of the nuclease. An example of a polypeptide comprising a TAT peptide operably linked to the amino-terminus of the nuclease and a superpositively charged GFP operably linked to the carboxy-terminus of the nuclease is provided herein as SEQ ID NO: 4. Polypeptide sequences that are at least about 75% identical to SEQ ID NO: 3 or SEQ ID NO: 4 are also provided. For example, polypeptide sequences that are at least about 75%, 80%, 85%, 90%, 95%, 99% or any percentage in between are also provided.

The nuclease can also be operably linked to a supercharged protein and one or more negatively charged peptides, for example, a negatively charged peptide of about 10 to about 25 amino acids in length, for example, SEQ ID NO: 50, can be operably linked to the carboxy-terminus of the site-directed nuclease. For example,and not to be limiting, a superpositively charged protein can be operably linked to the carboxy-terminus of the nuclease and a negatively charged peptide can be operably linked to the carboxy-terminus of the superpositively charged protein.

As used throughout, recombination is a process of exchange of genetic information between two polynucleotides. Homology-directed repair (HDR) refers to DNA repair that takes place, for example, during repair of double-strand breaks in cells. This process requires nucleotide sequence homology and uses a donor molecule, for example, a single stranded or a double stranded nucleotide sequence as a template for repair of a target genomic sequence, i.e., the genomic sequence with the double-strand break, and leads to the transfer of genetic information from the donor to the target genomic sequence. Homology-directed repair can result in a modification of the sequence of the target genomic sequence. For example, HDR can result in an insertion, a deletion or a mutation in the target genomic sequence. Part or all of the sequence of the donor polynucleotide can be incorporated into the target DNA. It is also contemplated that the donor polynucleotide, a portion of the donor polynucleotide, a copy of the donor polynucleotide, or a portion of a copy of the donor polynucleotide integrates into the target DNA.

As used throughout, by non-homologous end joining (NHEJ) is meant the repair of double-strand breaks in DNA by direct ligation of the break ends to one another without the need for a homologous template (in contrast to homology-directed repair, which requires a homologous sequence to guide repair).

The complexes and methods provided herein can be used to correct any mutation in a target DNA by HDR. For example, and not to be limiting, the complexes can be used to replace an incorrect nucleotide sequence with a correct nucleotide sequence (e.g., to restore function to a target polynucleotide sequence that is impaired due to a loss of function mutation, i.e., a SNP) at a specific site in the genome. These mutations can be associated with an autoimmune disorder, a genetic disease, a blood disorder, a T cell disorder, a monogenic disorder, cancer, a neurodegenerative disease, a cardiovascular disease or an infectious disease, to name a few. For example, and not to be limiting, the complexes and methods provided herein can be used to correct a mutation associated with sickle cell disease (i.e., a mutation in a hemoglobin gene, for example, a GAG to GTG mutation at codon 6 of the beta-globin gene that results in a glutamic acid to valine substitution), severe combined immunodeficiency (SCID) (for example, a mutation in JAK3), beta thalassemia or Wiskott-Aldrich Syndrome.

Correction of single mutations or multiple mutations can be performed with one or more complexes. The complexes and methods provided herein can also be used to insert sequences into a specific site in the genome to correct a deletion, as opposed to making a correction or a substitution.

The complexes and methods provided herein can also be used to insert a nucleotide sequence that encodes an a functional polypeptide into a specific site in the genome of the cell, in order to express the functional polypeptide in the cell. The functional polypeptide can be a polypeptide that is endogenous (i.e., normally expressed by the cell) or exogenous to the cell (i.e. not normally expressed by the cell). For example, chimeric antigen receptor (CAR) sequences can be inserted into the genome of a T cell precursor in order to generate cancer specific T cells for the treatment of cancer. In another example, the complexes and methods provided herein can be used to inhibit the activity of a gene at a specific site in the genome of the cell. For example, the complexes and methods provided herein can be used to insert sequences into the CXCR4 or CCR5 receptor to treat or prevent HIV infection.

The complexes provided herein can modify or alter target DNA with surprisingly high efficiency as compared to conventional CRISPR/Cas systems. The efficiency of alteration in a population of cells can be at least about 5%, 10%, 15%, 20%, 25%, 30%, 35%, 40%, 45%, 50%, 55%, 60%, 65%, 70%, 75% or 80% or higher or any percentage in between these percentages. The efficiency of alteration can also be greater than or equal to about 80%. Therefore, also provided herein are populations of cells, wherein at least 5%, 10%, 15%, 20%, 25%, 30%, 35%, 40%, 45%, 50%, 55%, 60%, 65%, 70%, 75% or 80% or higher or any percentage in between are altered. For example, a mutation associated with sickle cell disease or another disorder has been corrected. If a population of cells comprising a mutation associated with sickle cell disease is contacted with a CRISPR/Cas complex described herein and the mutation is corrected in about 5% of the cells, the efficiency of modification or alteration is about 5%. Optionally, a population of cells wherein the mutation associated with sickle cell disease is corrected in about 30% of the cells, including, for example, 27%, 28% and 29% is sufficient to treat sickle cell disease, upon transplantation in a subject with sickle cell disease. Optionally, a mutation associated with sickle cell disease is corrected in about 40%, 50%, 60%, 70%, 80%, 90% or higher or any percentage in between, of the cells in the population.

In addition to altering the target DNA with high efficiency, the complexes provided herein can also increase the ratio of HDR to NHEJ in a population of cells contacted with the complex. The HDR/NHEJ ratio can be from about 10 to about 0.5. For example, the HDR/NHEJ ratio can be about 10, 9, 8, 7, 6, 5, 4, 3, 2, 1, 0.5 or less or any ratio in between these ratios. In addition to high efficiency of correction and high rate of HDR to NHEJ, the cell survival rate for corrected cells can be at least about 50%, 60%, 70%, 80%, 90% or higher and any percentage in between.

Any cell(s) can be modified or derived using the complexes described herein. Introduction of the complex into the cells can be cell cycle dependent or cell cycle independent. Methods of synchronizing cells to increase the proportion of cells in a particular phase, for example, the S-phase, are known in the art. See, for example, Takahashi et al. "Efficient introduction of a gene into hematopoietic cells in S-phase by electroporation," *Exp. Hematol.* 19 (5):343-346 (1991). Depending on the type of cell to be modified, one of skill in the art can readily determine if cell cycle synchronization is necessary.

The cell(s) can be a eukaryotic cell, for example, a mammalian cell. The cell can also be prokaryotic or a plant cell. The cell can be a human cell. The cell can be a germ cell, a somatic cell, a stem cell, a precursor cell or a progenitor cell. The precursor cell can be, for example, a pluripotent stem cell or a multipotent stem cell, like a hematopoietic stem cell. As used throughout, pluripotent cells include induced pluripotent stem cells. Methods of making induced pluripotent stem cells and known in the art and described in the Examples. The cell can also be CD34+ cell, optionally derived from an induced pluripotent stem cell. The CD34+ cell can be selected from the group consisting of a primary CD34+ hematopoietic progenitor cell, a CD34+ peripheral blood cell, a CD34+ cord blood cell and a CD34+ bone marrow cell. The cell can also be a primary cell, for example, a primary CD34+ hematopoietic progenitor cell. The cells are cells that are not cancer cells, cells that are not tumor cells or cells that are not transformed cells. Cells can be screened before or after correction for evidence of undesirable genetic characteristics. Further provided is a cell comprising any of the complexes described herein. The cell can be in vitro, ex vivo or in vivo.

Further provided is a method of site-specific modification of a target DNA in a population of cells comprising introducing into the cells any of the complexes described herein, wherein the complex is introduced into the cells under conditions that allow homology-directed repair (HDR) and integration of a donor nucleotide, for example, a ssODN or double stranded nucleotide sequence into the target DNA. The complex can be introduced into the cell via nucleoporation. Methods for nucleoporation are known in the art. See, for example, Maasho et al. "Efficient gene transfer into the human natural killer cell line, NKL, using the amaxa nucleofection system," *Journal of Immunological Methods* 284 (1-2): 133-140 (2004); and Aluigi et al. "Nucleofection is an efficient non-viral transduction technique for human bone marrow derived mesenchymal stem cells," *Stem Cells* 24 (2): 454-461 (2006)), both of which are incorporated herein in their entireties by this reference.

In some of the methods provided herein, the donor nucleotide, for example, a ssODN or a double stranded nucleotide sequence integrates into a target DNA and corrects a mutation in the target DNA. In the methods provided herein the ratio of HDR to NHEJ in a population of cells is increased relative to other CRISPR-Cas9 delivery methods. The HDR/NHEJ ratio can be from about 10 to about 0.5. For example, the HDR/NHEJ ratio can be about 10, 9, 8, 7, 6, 5, 4, 3, 2, 1, 0.5 or less or any ratio in between these ratios. In the methods provided herein, the efficiency of alteration by HDR can be at least about 5%, 10%, 15%, 20%, 25%, 30%, 35%, 40%, 45%, 50%, 55%, 60%, 65%, 70%, 75%, 80% or greater or any percentage in between these percentages. The efficiency of alteration by HDR can also be greater than or equal to about 80%. For example, if a population of cells comprising a mutation associated with sickle cell anemia is contacted with a CRISPR/Cas complex described herein and the mutation is corrected in about 5% of the cells, the efficiency of alteration by HDR is about 5%. The population of cells can be obtained from the subject having a disorder such that at least about 5%, 10%, 15%, 20%, 25%, 30%, 35%, 40%, 45%, 50%, 55%, 60%, 65%, 70%, 75% or 80% or greater or any percentage in between these percentages, of the cells undergo HDR to correct a mutation associated with the disorder. In some cases greater than 80% of the cells from the subject will undergo HDR to correct a mutation associated with the disorder. In the methods described herein, between about 50% and 99% of the cells survive after introduction of the complex. For example, great than about 50%, 60%, 70%, 80%, 90%, 95%, 99% or any percentage in between these percentages, of corrected cells survive after introduction of the complex.

Further provided is a method of treating a disease associated with a mutation in the genomic sequence encoding hemoglobin in a subject comprising: (a) introducing into a population of cells obtained from the subject a complex comprising (1) a guide RNA (gRNA) comprising a first nucleotide sequence that hybridizes to a target DNA in the genome of a cell, wherein the target DNA is a hemoglobin gene that comprises a mutation, and a second nucleotide sequence that interacts with a site-directed nuclease; (2) a recombinant site-directed nuclease operably linked to a supercharged protein, wherein the site-directed nuclease comprises an RNA-binding portion that interacts with the second nucleotide sequence of the guide RNA and wherein the site-directed nuclease specifically binds and cleaves the target DNA to create a double stranded break; and (3) a single-stranded donor oligonucleotide (ssODN) that hybridizes to a genomic sequence flanking the double stranded break in the target DNA and integrates into the target DNA to correct the mutation in hemoglobin gene; and (b) transplanting the corrected cells into the subject.

In the methods for treating a disease associated with a mutation in the genomic sequence encoding hemoglobin in a subject, for example, sickle cell anemia, the subject with sickle cell anemia can optionally be a transfusion dependent subject or a subject with at least one silent infarction. The subject can also be less than about twelve months, eleven months, ten months, nine months, eight months, seven months, six months, five months, four months, three months, two months, or one month in age. As infants are routinely screen for sickle cell disease, infants can be treated before symptoms of the disease manifest. The methods provided herein can further comprise diagnosing a subject with a disorder, for example, sickle cell disease.

As set forth above, cells can be obtained from the subject with the disease or from a related donor. For example, bone marrow cells can be obtained or harvested from the subject. Bone marrow harvesting involves collecting stem cells with a needle placed into the soft center of the bone, the marrow. Bone marrow can be harvested for example, from the hip bones or sternum of the subject. From about 500 ml to about 1 liter of bone marrow can be obtained from the subject.

In any of the methods provided herein the cell(s) can be a eukaryotic cell, for example, a human cell. The cell can be a germ cell, a stem cell, a precursor cell. The precursor cell can be, for example, a pluripotent stem cell or a hematopoietic stem cell. As used throughout, pluripotent cells include induced pluripotent stem cells. Methods of making induced pluripotent stem cells and known in the art and described in the Examples. The cell can also be CD34+ cell. The CD34+ cell can be selected from the group consisting of a primary CD34+ hematopoietic progenitor cell, a CD34+ peripheral blood cell, a CD34+ cord blood cell and a CD34+ bone marrow cell. The cell can also be a primary cell, for example, a primary CD34+ hematopoietic progenitor cell. The cells are that are not cancer cells, cells that are not tumor cells or cells that are not transformed cells. The cell can be in vitro or ex vivo. The cells can also be in a pharmaceutically acceptable composition.

The methods provided herein can further comprise culturing the cells corrected with HDR. For example, the cells can be cultured under conditions for expansion or under conditions that promote differentiation of the corrected cells into T-cells. For example, and not to be limiting, using the methods provided herein, after a mutation has been corrected in induced pluripotent stem cells via HDR, the corrected cells can be co-cultured with human bone marrow stromal cells to generate CD34+ cells. The CD34+ cells can then be cultured under conditions that differentiate the CD34+ cells into T cells.

The methods provided herein can further comprise screening the corrected cells for the proper correction, other mutations, or NEJ prior to transplantation. Optionally cells can be screened to detect cells with one or more corrections.

In the methods provided herein, the cells can be transplanted into the subject after modification, for example, after correction of a mutation by HDR. The cells can be transplanted into the subject with or without differentiation. For example, modified hematopoietic stem cells (HSCs) can be administered in a bone marrow transplant, wherein the HSCs are allowed to differentiate and mature in vivo in a subject Alternatively, the modified cells can be differentiated into a desired population of cells prior to transplantation.

As used herein, transplanting, introducing or administering cells to a subject refers to the placement of cells into a subject. For example, the cells described herein comprising a target DNA sequence corrected or modified according to the methods described herein can be transplanted into a subject, by an appropriate route which results in at least partial localization of the transplanted cells at a desired site. The cells can be implanted directly to the desired site, or alternatively can be administered by any appropriate route which results in delivery to a desired location in the subject where at least a portion of the implanted cells remain viable. For example, the cells can be administered systemically, via intravenous infusion. The period of viability of the cells after administration to a subject can be as short as a few hours, e.g. twenty-four hours, to a few days, to as long as several years.

For ex vivo methods, cells can be autologous cells, i.e., a cell or cells taken from a subject who is in need of modification of a target DNA in the cell or cells (i.e., the donor and recipient are the same individual). As described herein, the modification can be, for example correction of a mutation, insertion of a sequence that inhibits activity of a protein or insertion of a sequence that increases expression of a protein, for example, insertion of a sequence encoding a chimeric antigen receptor that can be used to target cancer cells. Autologous cells can be used to avoid immunological reactions that can result in rejection of the cells. In other words, when using autologous cells, the donor and recipient are the same subject. Alternatively, the cells can be heterologous, e.g., taken from a donor, preferably a related donor. The second subject can be of the same or different species. Typically, when the cells come from a donor, they will be from a donor who is sufficiently immunologically compatible with the recipient to reduce the chances of transplant rejection, and/or to reduce the need for immunosuppressive therapy. The cells can also be obtained from a xenogeneic source, i.e., a non-human mammal that has been genetically engineered to be sufficiently immunologically compatible with the recipient, or the recipient's species. Any of the methods of treating a disorder described herein can further comprise administering one or more immunosuppressants to the subject.

In the methods involving transplantation, a subject optionally undergoes myeloablative therapy prior to transplantation of any of the cells described herein. The myeloablative therapy can include administering one or more doses of chemotherapy, radiation therapy, or both, that results in severe or complete depletion of healthy bone marrow cells. In another example, the subject can undergo submyeloablative therapy that includes administering one or more doses of chemotherapy, radiation therapy, or both, that depletes a portion of the healthy bone marrow cells. The cells can also be transplanted into subjects that have undergone nonablative chemotherapy. For example, the cells can be transplanted into a subject that has been treated with Busulfan, Fludarabine and/or Treosulfan.

In the methods involving transplantation, an effective dose or amount of corrected cells is administered to the subject. The terms effective amount and effective dosage are used interchangeably. The term effective amount is defined as any amount necessary to produce a desired physiologic response. In some methods, about $1\times10^6$ to about $7\times10^6$ corrected cells/kg can be administered, but this amount can vary depending on the associated disorder.

The percentage of corrected cells that Effective amounts and schedules for administering the cells may be determined empirically, and making such determinations is within the skill in the art. The dosage ranges for administration are those large enough to produce the desired effect (e.g., treatment of a disease, for example, sickle cell anemia). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and the agent can be administered in one or more dose administrations daily, for one or multiple days as needed.

As used throughout, a subject can be a vertebrate, more specifically a mammal (e.g., a human, horse, cat, dog, cow, pig, sheep, goat, mouse, rabbit, rat, and guinea pig). The term does not denote a particular age or sex. Thus, adult and newborn subjects, whether male or female, are intended to be covered. As used herein, patient or subject may be used interchangeably and can refer to a subject with or at risk of developing a disorder. The term patient or subject includes human and veterinary subjects.

As used herein the terms treatment, treat, or treating refers to a method of reducing one or more of the effects of the disorder or one or more symptoms of the disorder, for example, sickle cell disease, by eliciting an immune response in the subject. Thus in the disclosed method, treatment can refer to a 10%, 20%, 30%, 40%, 50%, 60%, 70%, 80%, 90%, or 100% reduction in the severity of sickle cell disease and other disorders. For example, a method for treating sickle cell disease is considered to be a treatment if there is a 10% reduction in one or more symptoms of the infection in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disorder or symptoms of the disorder.

Also provided is a method of correcting a mutation associated with a T-cell disorder comprising introducing into a population of cells obtained from a subject with the T-cell disorder a complex comprising: (a) a guide RNA (gRNA) comprising a first nucleotide sequence that hybridizes to a target DNA in the genome of a cell, wherein the target DNA comprises the mutation associated with the T-cell disorder, and a second nucleotide sequence that interacts with a site-directed nuclease; (b) a recombinant site-directed nuclease operably linked to a supercharged protein, wherein the site-directed nuclease comprises an RNA-binding portion that interacts with the second nucleotide sequence of the gRNA and wherein the site-directed nuclease specifically binds and cleaves the target DNA that comprises the mutation associated with the T-cell disorder to create a double stranded break in the target DNA; and (c) a single stranded donor oligonucleotide (ssODN) comprising a third nucleotide sequence that hybridizes to a genomic sequence flanking the double stranded break in the target DNA and that integrates into the target DNA to correct the mutation associated with the T-cell disorder, wherein the complex is introduced into the cell under conditions that allow homology-directed repair (HDR) to correct the mutation associated with the T-cell disorder.

In the methods provided herein, the target DNA comprising a mutation associated with a T-cell disorder can be a target DNA that encodes a protein associated with T-lymphocyte development. For example, the target DNA can encode JAK3. Such corrected cells can be used, for example, in the treatment of SCID.

In addition to correcting mutations in the genome of a cell, the complexes and methods provided herein can also be used to insert functional polypeptides at specific sites in the genome of a cell, such that the polypeptide is expressed by the cell. The polypeptide can be expressed in the cell or on the cell surface.

Also provided is a method of making tumor-specific T-cell precursor cells comprising introducing into a population of T-cell precursor cells a complex comprising: (a) a guide (gRNA) comprising a first nucleotide sequence that hybridizes to a target DNA in the genome of the T cell precursor cells and a second nucleotide sequence that interacts with a site-directed nuclease; (b) a recombinant site-directed nuclease operably linked to a supercharged protein, wherein the site-directed nuclease comprises an RNA-binding portion that interacts with the second nucleotide sequence of the gRNA and wherein the site-directed nuclease specifically binds and cleaves the target DNA to create a double stranded break; and (c) donor nucleotide sequence comprising a third nucleotide sequence that encodes a chimeric antigen receptor (CAR) and a fourth nucleotide sequence that hybridizes to a genomic sequence flanking the double stranded break in the target DNA, wherein the complex is introduced into the T-cell precursor cells under conditions that allow homology-directed repair (HDR) and integration of the third nucleotide sequence into the target DNA to form modified T-cell precursor cells that express the CAR.

The T cell precursor cells can be obtained from a subject with cancer. As set forth above, the HDR/NHEJ ratio can be from about 10 to about 0.5. For example, the HDR/NHEJ ratio can be about 10, 9, 8, 7, 6, 5, 4, 3, 2, 1, 0.5 or any ratio in between these ratios. In the methods provided herein, the efficiency of alteration by HDR can be at least about 5%, 10%, 15%, 20%, 25%, 30%, 35%, 40%, 45%, 50%, 55%, 60%, 65%, 70%, 75%, 80% or any percentage in between these percentages. The efficiency of alteration by HDR can also be greater than or equal to about 80%. For example, when using the methods described herein, if a nucleotide sequence encoding an functional polypeptide, for example, a nucleotide sequence that encodes a CAR, is inserted in about 5% of the cells, the efficiency of alteration by HDR is about 5%. The population of cells can be obtained from the subject that has cancer such that at least about 5%, 10%, 15%, 20%, 25%, 30%, 35%, 40%, 45%, 50%, 55%, 60%, 65%, 70%, 75% or 80% or any percentage in between these percentages, of the cells undergo HDR to insert a nucleotide sequence that encodes a chimeric antigen receptor (CAR)

and form cells that express the CAR. In some cases greater than 80% of the cells from the subject will undergo HDR to correct a mutation associated with the disorder.

The modified T-cell precursor cells that express the CAR can be transplanted into a subject with cancer. As used herein, cancer is a disease characterized by the rapid and uncontrolled growth of aberrant cells. Cancer cells can spread locally or through the bloodstream and lymphatic system to other parts of the body. Examples of cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The modified T-cell precursor cells that express the CAR exhibit anti-tumor immunity when the antigen binding domain binds to its corresponding antigen.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1

Correction of SCID by CRISPR/Cas9 Enhanced Gene Replacement

Mutations of the Janus family kinase JAK3 gene cause severe combined immunodeficiency (SCID). JAK3 deficiency in humans is characterized by the absence of circulating T cells and natural killer (NK) cells with normal numbers of poorly functioning B cells (T−B+NK−). As shown herein, using SCID patient-specific induced pluripotent stem cells (iPSCs) and a T cell in vitro differentiation system, a complete block in early T cell development of JAK3-deficient cells was demonstrated. Correction of the novel JAK3 mutation by CRISPR/Cas9 enhanced gene replacement restores normal T cell development, including the production of mature T-cell populations with a broad T Cell Receptor (TCR) repertoire. Whole genome sequencing of corrected cells demonstrated no CRISPR/Cas9 off-target modifications. Thus, provided herein is a novel approach for the study of human lymphopoiesis and a method for gene replacement therapy in humans with immunodeficiencies.

Allogeneic hematopoietic stem cell (HSC) transplantation is currently the only established therapy for SCID; however, delayed immune recovery and risk of graft-vs-host disease present significant risks. Treatment by retroviral-based gene therapy has been successfully demonstrated for X-linked SCID. However, severe adverse effects of insertional mutagenesis have been observed with retroviral gene therapy. Self-inactivating lentiviral vectors have been used effectively in recent clinical trials, but long-term follow-up is needed to thoroughly address safety concerns.

Provided herein is an alternative therapeutic strategy in which patient-specific induced pluripotent stem cells (iPSCs) are derived, and disease-causing mutations are corrected by gene replacement using a CRISPR-Cas9 complex. These corrected iPSCs could optionally be differentiated into hematopoietic progenitors for transplantation into patients to treat the disease (Hanna et al., "Treatment of sickle cell anemia mouse model with iPS cells generated from autologous skin," *Science* 318: 1920-1923 (2007)). As shown herein, differentiation of JAK3-deficient human T cells is blocked at an early developmental stage. Also demonstrated is that correction of the human JAK3 mutation by CRISPR/Cas9 enhanced gene replacement restores the differentiation potential of early T cell progenitors. These corrected progenitors are capable of producing NK cells and mature T cell populations expressing a broad repertoire of T-cell antigen receptors (TCR). These studies establish a powerful system for determining the mechanism of immunodeficiency in human SCID patients and for testing pharmacological and genetic therapies for the disorder.

Patient Information

The male patient was enrolled in an Institutional Review Board-approved study in accordance with the Declaration of Helsinki. The family history was negative for immune deficiencies. For the first 8 months of age he had poor weight gain, diarrhea, and recurrent bronchiolitis requiring frequent hospitalization. He was admitted to the hospital at 8 months of age with severe respiratory distress and oral thrush. Bronchoscopy with bronchial alveolar lavage demonstrated bacterial (pseudomonas, H flu, S. pneumonia) and viral organisms (respiratory syncytial virus). Immunologic evaluations demonstrated severe hypogammaglobulinemia, with an IgE<3, IgA<4, IgG=29, IgM=26. Immune phenotyping of peripheral blood demonstrated complete absence of CD3+ T cells and NK cells, though B cells were present (absolute B cell count=875). Mitogen studies demonstrated a complete lack of response to concanavalin A, poke weed mitogen and phytohemagglutinin A. The diagnosis of SCID was confirmed by genetic testing, with a homozygous C>T nucleotide substitution in exon 14 of the JAK3 gene, resulting in the replacement of an arginine codon (CGA) with a stop codon (TGA) at amino acid position 613. This is the first report linking this JAK3 variant (r5149316157) to a clinical case of SCID. The patient underwent a reduced intensity conditioning matched unrelated bone marrow transplant, and is doing well now two years off therapy with complete immune reconstitution.

Human iPSC Reprogramming and Characterization

For iPSC induction, $5 \times 10^4$ primary keratinocytes were seeded into one well of a 6-well plate. On the following day, keratinocytes were transduced with 1 mL of virus supernatant and 1 mL of human keratinocyte medium containing polybrene at a final concentration of 4 μg/mL. The keratinocytes were spinfected at 800× g for 45 minutes (day 1). The transduction procedure was repeated again the next day.

On day 3, cells were changed to fresh human keratinocyte medium and cultured for two more days. On day 5, the keratinocytes were trypsinized and transferred to a 10 cm dish pre-seeded with mitomycin C-treated murine embryonic fibroblasts (MEFs) and cultured in human keratinocyte medium. On day 7, cells were changed to human ES medium and continuously cultured in the same dish for 3-4 weeks. ES medium was changed daily. Potential iPSC colonies were visible after 2-3 weeks. These colonies were individually picked and expanded on MEFs for analysis. To remove the integrated lentiviral and polycistronic sequences, iPSCs were infected with a Cre-expressing adenovirus (rAd-Cre-IE). Individual colonies were picked and Cre-mediated removal of foxed sequences was verified by PCR using the primers gctaattcactcccaaagaagacaag (SEQ ID NO: 5) and cttcagcaagccgagtcctg (SEQ ID NO: 6).

Generation of CD34+ Cells and T Cells with OP9 Co-Culture

The procedure was described previously (Chang et al., "Broad T-cell receptor repertoire in T-lymphocytes derived from human induced pluripotent stem cells," PloS one 9, e97335 (2014)). This method was used with the following modifications. Cultures of hiPSCs in one well of a 6 well plate were treated as described by Ohnuki et al (Ohnuki M, "Generation and characterization of human induced pluripotent stem cells. Curr Protoc Stem Cell Biol Chapter 4: Unit 4 A 2 (2009)) with CTK solution to make small cell clumps. Cell clumps were then transferred to a 10 cm plate that was pre-seeded with 2-day old OP9 cells in α-MEM-based medium containing 10% FBS, 1× penicillin/streptomycin and 100 µM mono-thioglycerol. The medium was changed every other day, and cells were cultured for 18 days without splitting. After 18 days of co-culture, cells were harvested by treating with dissociation solution (0.15% collagenase IV and 0.015% hyaluronidase in α-MEM medium) for about 30 minutes and followed by 0.25% trypsin for another 30 minutes. CD34+ cells were then purified on anti-CD34+ magnetic beads (MicroBead Kit; Miltenyi Biotec, Bergisch Gladbach, Germany). For T cell differentiation, these CD34+ cells were plated onto OP9-DL4 cells and cultured with α-MEM medium containing 20% FBS, 5 ng/mL hFlt3-L, 5 ng/mL hIL-7, and 10 ng/mL hSCF. The medium was changed every other day, and cells were transferred to new OP9-DL4 plates every 4 days.

T Cell Stimulation

In vitro derived T cells from hiPSCs were stimulated by incubation with CD3/28 beads (Invitrogen, Carlsbad, Calif.) according to the manufacturers' protocol for 3 days prior to analysis by flow cytometry, as previously described (Chang et al., 2014).

Flow Cytometry

Cells were harvested and washed before analysis with an LSRFortessa cell analyzer (BD Bioscience, San Jose, Calif.). For cell surface staining, propidium iodide (PI, Sigma-Aldrich, St. Louis, Mo.) was used to exclude dead cells. For apoptosis assay, harvested cells were first stained with cell surface antibodies for 30 min. After washing once with 1× PBS, the cells were resuspended in 100 µL of Annexin Binding Buffer (Invitrogen, Carlsbad, Calif.) containing Annexin V-647 (Invitrogen, Carlsbad, Calif.) and PI and incubated for 15 min before adding 400 µL of Annexin Binding Buffer with PI. Antibodies were obtained from BD Biosciences unless otherwise indicated: CD3 (Percp-Cy5-5, clone UCHT1), CD4 (PE-Cy7, clone SK3), CD7 (APC, BV510, clone M-T701), CD8 (APC-Cy7, clone SK1), CD16 (PE, clone B73.1), CD25 (FITC, clone 2 A3), CD34 (PE-Cy7, clone WM59), CD43 (PE, clone 1 G10), CD56- PE (clone MY31), CD69 (FITC, clone L78), NKG2 D-PE (clone 1 D11), TCR-αβ (FITC, PE, clone T10 B9.1 A-31), TCR-Vδ1-FITC (Fisher Scientific, Pittsburgh, Pa., Clone TS8.2), TCR-Vδ2-PE (clone B6), TCRVγ9-FITC (clone B3), TNF-α-PE-Cy7 (clone MAB11), Beta Mark TCR Repertoire Kit (Beckman Coulter, Atlanta, Ga.).

Vector Construction

The polycistronic OSKM vector was previously described (Chang et al.,"Polycistronic lentiviral vector for "hit and run" reprogramming of adult skin fibroblasts to induced pluripotent stem cells," Stem cells 27: 1042-1049 (2009)). The Lenti-hDL4-mCherry plasmid was constructed by cloning a PCR-amplified human DL4 cDNA (Open Biosystems, LaFayette, Colo.), an IRES fragment (Open Biosystems) and mCherry cDNA into a lentiviral vector (pDL171) which contains the EF1α promoter. PCR reactions were performed using PrimeStar polymerase (Takara, Mountain View).

To construct CRISPR plasmids, gRNA oligos were designed and introduced into pX330 and pX335 plasmids following the Zhang lab protocol (Addgene, Cambridge, Mass.). To construct the JAK3 repair plasmid, wild type human genomic DNA was PCR amplified using JAK3 primer sets (5' arm: gtcgacgtcgacgctcagtgaagctgaagtat-tccttctgcttcacagggcgaccactac (SEQ ID NO: 7) and att-taaatcctcccctcgaacccttaccaaactcctatgcatactacag (SEQ ID NO:8); 3' arm: ttaattaattaattagcattttaggttcaggttgt-gagaacactagaagagaacaagtca (SEQ ID NO: 9) and gtatacgtatacgcatacctggagaggggacaaggtcttgagatgcgagggt (SEQ ID NO: 10). After digesting with enzymes (5' arm: SalI and SwaI; 3' arm: PacI and BstZ17 I), the PCR products were cloned into a plasmid containing a LoxP-PGK-Neo-LoxP fragment. All of the oligos used in this study were synthesized by Integrated DNA Technologies (IDT, Coralville, Iowa). To construct the BCL2 lentiviral plasmid, a primer set (forward: agccaccttaattaagccaccatggcgcacgctgg-gagaacggggtacgata (SEQ ID NO: 11) and reverse: taacagagagaagttcgtggctccggatcccttgtggcccaga-taggcacccagggtgat (SEQ ID NO: 12)) was used to amplify the human BCL2 cDNA (Open Biosystems) fragment. The product was linked with GFP through a 2 A sequence by PCR and cloned into the pDL171 vector. gRNA-F1 caccgTG AGA TAC AGA TAC AGA CA (SEQ ID NO: 13) gRNA-R1 aaacTGT CTG TAT CTG TAT CTC AC (SEQ ID NO: 14) gRNA-F2 caccgAAT GAT TTG CCT GGA ATG CC (SEQ ID NO: 14) gRNA-R2 aaacGGC ATT CCA GGC AAA TCA TTc (SEQ ID NO: 15) gRNA-F3 caccgCAG CCT AGG CAA AGG CCT GC (SEQ ID NO: 16) gRNA-R3 aaacGCA GGC CTT TGC CTA GGC TGc (SEQ ID NO: 17) gRNA-F4 caccgTGC CAA CAG AAC TGC CTG AT (SEQ ID NO: 18) gRNA-R4 aaacATC AGG CAG TTC TGT TGG Cac (SEQ ID NO: 19) gRNA-F5 caccgAC CAG GGT GCA AGT GTG GA (SEQ ID NO: 20) gRNA-R5 aaacTCC ACA CTT GCA CCC TGG TC (SEQ ID NO: 21) gRNA-F6 caccgGCT CCT CAG CCT GGC ATT CA (SEQ ID NO: 22) gRNA-R6 aaacTGA ATG CCA GGC TGA GGA GC (SEQ ID NO: 23)

Cell Culture

IPSCs were cultured on mitomycin C-treated MEFs derived from E14.5 CF-1 embryos in ES cell media consisting of DMEM F-12 supplemented with 1× non-essential amino acids, 1× penicillin-streptomycin, 1× L-glutamine (all from Mediatech, Corning, N.Y.), 20% KnockOut Serum Replacement (Invitrogen), 2-βME (Sigma) and 5-10 ng/mL bFGF (Invitrogen). Human primary keratinocytes were cultured in DermaLife K Medium Complete Kit (LifeLine Cell Technology, Frederick, Md.). OP9 cells were purchased from ATCC and grown in α-MEM medium with 20% FBS and penicillin-streptomycin. OP9-DL4 cells were established by transducing OP9 cells with a lentivirus containing hDL4 and mCherry.

Virus Production

For preparation of lentivirus, 10 μg of the lentiviral vector, 2.5 μg of the envelope plasmid (pMDG), and 7.5 μg of the packaging plasmid (pCMBVdR8.9.1) were co-transfected into 5×106 293 T cells by Fugene 6 (Roche, Nutley, N.J. or Promega, Madison, Wis.). Virus-containing supernatant was collected 2 days after transfection and passed through a 0.45 μm filter.

Gene Targeting

IPSCs were treated with 0.25% trypsin for 5 minutes to generate single cell suspensions. After washing twice with 1× PBS, 1 to 2 million cells were mixed with 5 μg of JAK3 repair plasmid and 5 μg of pX330-JAK3 or pX335-JAK3 plasmids for Nucleofection (Human Stem Cell Nucleofector Kit, program A-023, Lonza, Alpharetta, Ga.) and plating onto MEFs. Two to four days later, hES medium containing 30 μg/mL of G418 was added to the plates to select for drug resistant colonies. The colonies were picked 3 to 4 weeks later and expanded for genomic DNA extraction. For PCR genotyping, a 5' primer set (tgctaaagcgcatgctccagact (SEQ ID NO: 24) and gtcttcatctcagggtcggct (SEQ ID NO: 25) and a 3' primer set (cctctctgtgcattatggcag (SEQ ID NO: 26) and gccttctatcgccttcttg (SEQ ID NO: 27)) were used. To remove the Neo selection marker, hiPSCs were infected with a Cre-expressing adenovirus (rAd-Cre-IE).

RT-PCR

Total RNA was isolated from in-vitro derived cells with Trizol reagent (Invitrogen, Carlsbad, Calif.). cDNA was synthesized with 0.5 to 2 μg of total RNA using Superscript First-strand Synthesis System (Invitrogen) according to the manufacturer's instructions. SYBR Green PCR Master Mix (Life Technologies, Carlsbad, Calif.) was used for qPCR according to the manufacturer's instructions. Primer sets used for qPCR are GAPDH (F: actcctccacctttgacgct (SEQ ID NO: 28), R: tcccctcttcaagggtctacatg (SEQ ID NO: 29)); PU.1 (F: gtgcaaaatggaagggtttc (SEQ ID NO: 30), R: ggagctccgtgaagttgttc (SEQ ID NO: 31)); GATA3 (F: tgtttcctttcactggccaca (SEQ ID NO: 32), R: aacggcaactggtgaacggta (SEQ ID NO: 33)); BCL11B (F: ggcgatgccagaatagatgccg (SEQ ID NO: 34), R: ccaggccacttggctcctctatctccaga (SEQ ID NO: 35)); RAG1 (F: ccttactgttgagactgcaatatcc (SEQ ID NO: 36), R: ctgaagtcccagtatatacttcacac (SEQ ID NO: 37)); RAG2 (F: cccagaagcagtaataatcatcgag (SEQ ID NO: 38), R: atgtgggatgtagtagatcttgc (SEQ ID NO: 39)); pTa (F: gggtcttacctcagcagttac (SEQ ID NO: 40), R: cctcacacagtgtgacgcag (SEQ ID NO: 41)); BCL2 (F: gactgagtacctgaaccggc (SEQ ID NO: 42), R: gggccaaactgagcagagtc (SEQ ID NO: 43)); BAX (F: aagaccagggtggttgggac (SEQ ID NO: 44), R: gtaagaaaaatgcccacgtc (SEQ ID NO: 45)); and JAK3 (F: agtcagacgtctggagcttc (SEQ ID NO: 46), R: gtgagcagtgaaggcatgagtc (SEQ ID NO: 47)). All values were normalized relative to GAPDH expression.

Whole Genome Sequencing and Analysis

DNA from iPSCs was sheared using a Covaris S2 Focused-ultrasonicator: 130 μL samples in microTUBEs were subjected to two 40-second cycles of 10% Duty Cycle, Intensity of 4, and 200 Cycles per Burst in Frequency Sweeping Mode. DNA Chip (DNA 1000 Kit; Agilent Technologies, Santa Clara, Calif.) analysis using an Agilent 2100 Bioanalyzer indicated an average fragment size of 400 bp. Library preparation was performed using an NEBNext Ultra DNA Library Prep Kit for Illumina (NEB #E7370), and the final library concentration was determined by qPCR using a KAPA Illumina Library Quantification Kit (KK4835; KAPA Biosystems, Wilmington, Ma.) and an Applied Biosystems ViiA 7 Real-Time PCR System (Life Technologies). Sequencing clusters were produced on the flow cell using an Illumina TruSeq PE Cluster Kit v313 cBot—HS (PE-401-3001) and an Illumina cBot. WGS was performed using an Illumina TruSeq SBS Kit v3—HS—200 cycles (FC-401-3001) and an Illumina HiSeq 2500 upgrade to generate 2×100 single-index paired-end reads for bioinformatic analysis. Probable off-target sites were identified by aligning the CRISPR/Cas9 guide sequences to the hg19 reference genome using EMBOSS fuzznuc software (v6.6.0.0) (Rice et al., "EMBOSS: the European Molecular Biology Open Software Suite," *Trends in Genetics*: TIG 16: 276-277 (2000)) and allowing for a maximum of three mismatches; 1193 sites were predicted for the first guide sequence (GTGAGATACAGATACAGACA) (SEQ ID NO: 48) and 257 sites for the second guide sequence (AATGATTGCCTGGAATGCC) (SEQ ID NO: 49). All of the reads from the WGS for each sample were mapped to the hg19 reference genome using the BWA (v0.7.5 a) mem algorithm (Li and Durbin, "Fast and accurate long-read alignment with Burrows-Wheeler transform," *Bioinformatics* 26: 589-595 (2010)) and duplicate reads were removed using Picard-tools (v1.100) (http://picard.sourceforge.net). Local realignment and base quality re-calibration were performed using GATK (v2.7-2) (McKenna et al., "The Genome Analysis Toolkit: a MapReduce framework for analyzing next-generation DNA sequencing data," *Genome research* 20: 1297-1303 (2010)). Both SNVs and indels were called using the GATK HaplotypeCaller. Additionally, SNVs and indels were separately re-calibrated as described in GATK Best Practices and quality filters were applied. The variants from the reference genome that were common to all four iPSC samples were excluded from CRISPR/Cas9 off-target analysis. The non-excluded variants were screened using Bedtools (v2.17.0) (Quinlan and Hall, "BEDTools: a flexible suite of utilities for comparing genomic features," Bioinformatics 26: 841-842 (2010)) to determine if they fell within the probable off-target sites. The analysis shows that none of these variants reside in the off-target sites and suggests these mutations were randomly accumulated. All of the functional variants (excluded and non-excluded) with a low allele frequency (<1%, dbSNP 138) were then annotated using the ANNOVAR software package and screened for known associations with diseases in HGMD and ClinVar (v20140902); additionally, all of the hits with a high CADD score (CADD>=20) were also screened for associations with complex diseases using the GWAS Catalog and COSMIC (v70). No validated disease-associated variants were identified in the databases queried. Of particular interest, the JAK3 C1837T (p.R613X) mutation was also not validated to associate with a disease, though the SNP (r5149316157) is predicted to be significantly deleterius, with a GERP score of 3.85 and a CADD score (CADD phred-like score) of 38. Therefore, the JAK3 C1837 T variant was associated for the first time with a clinical case of SCID.

Accession Codes

The WGS data can be accessed at the NCBI SRA database with the accession number SRP056149.

Figure 1B:
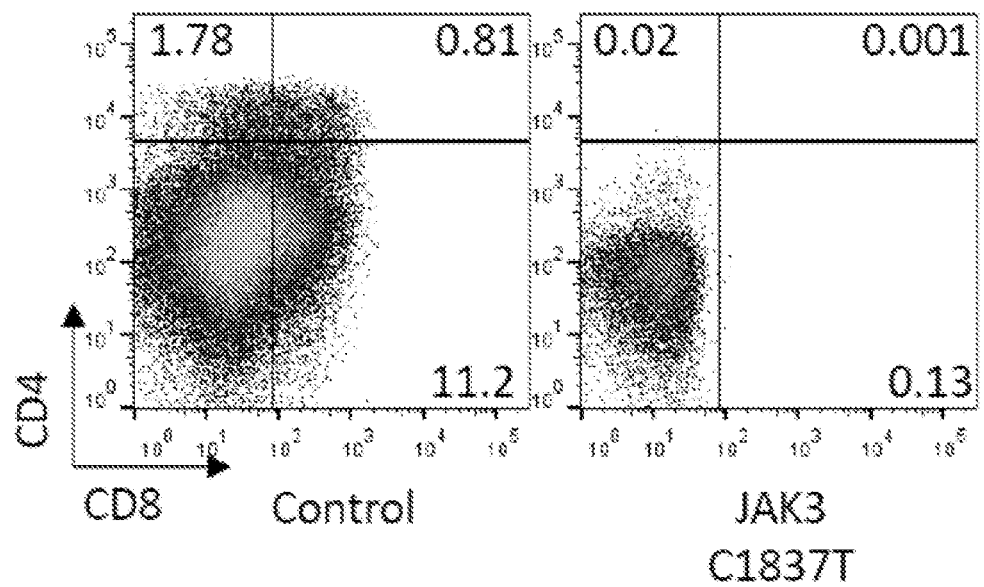
Figure 1C:
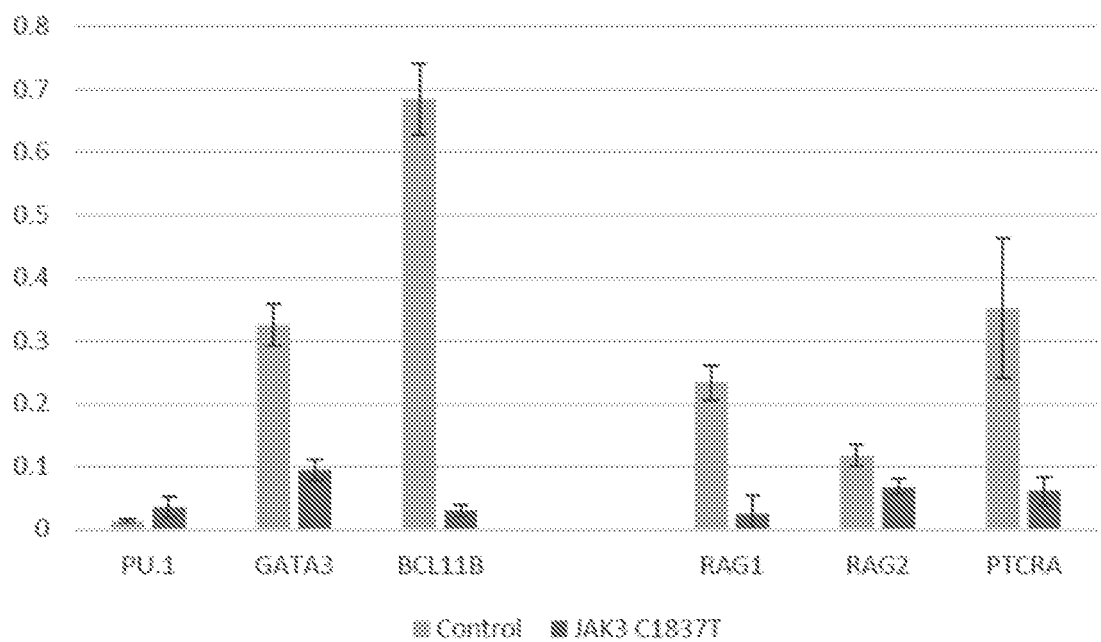
Figure 2A:
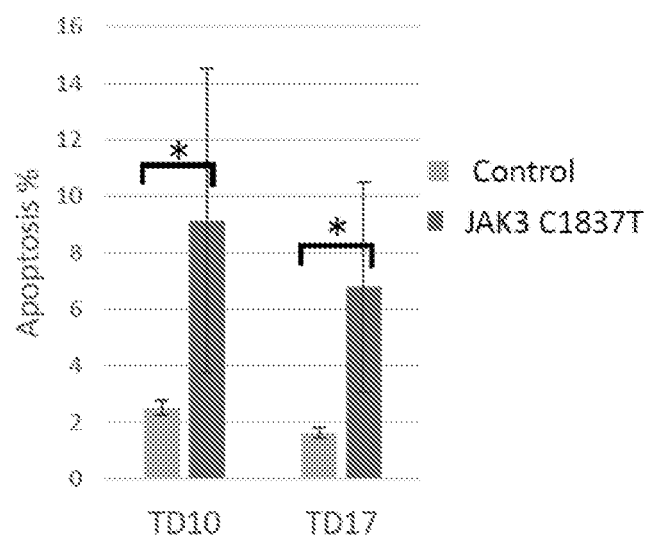
FIGS. 2A-2C show that BCL2 partially rescues T cell developmental defects in JAK3-deficient, in-vitro derived cells.
Figure 2B:
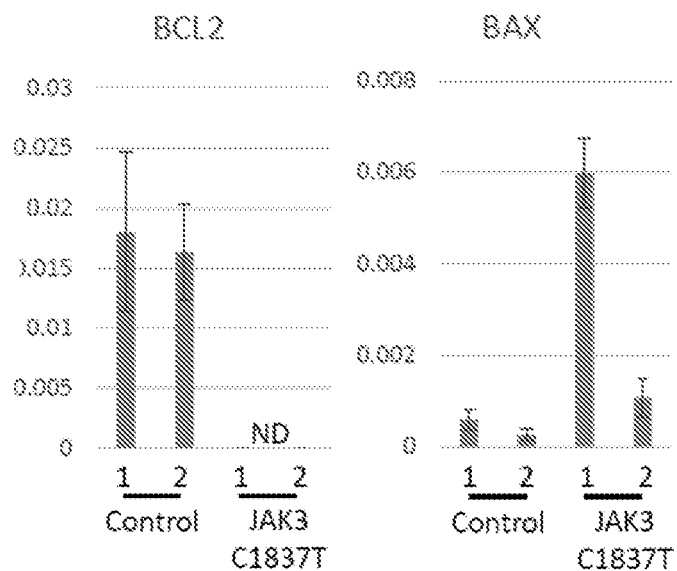
Figure 2C:
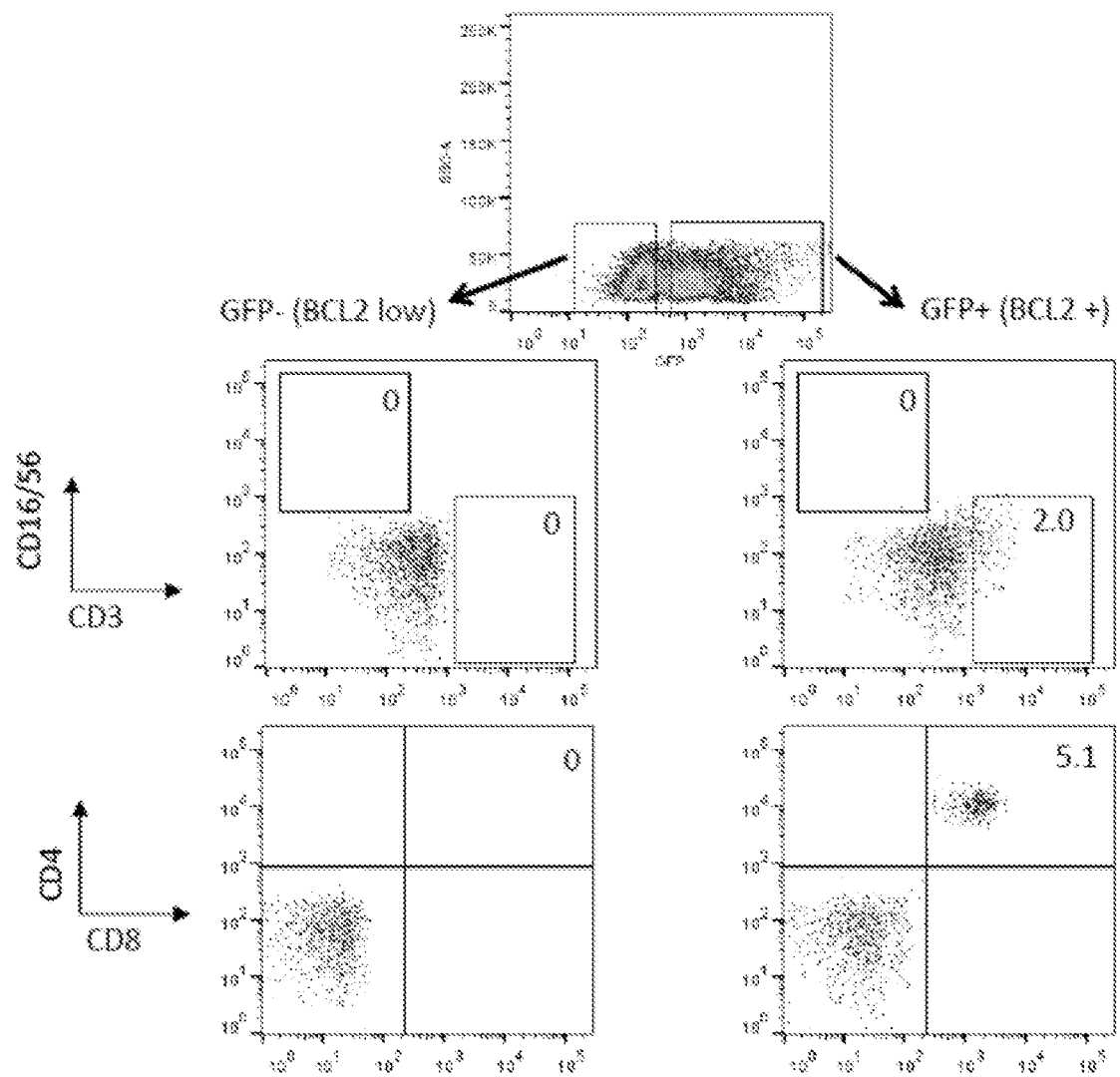
Figure 4A:
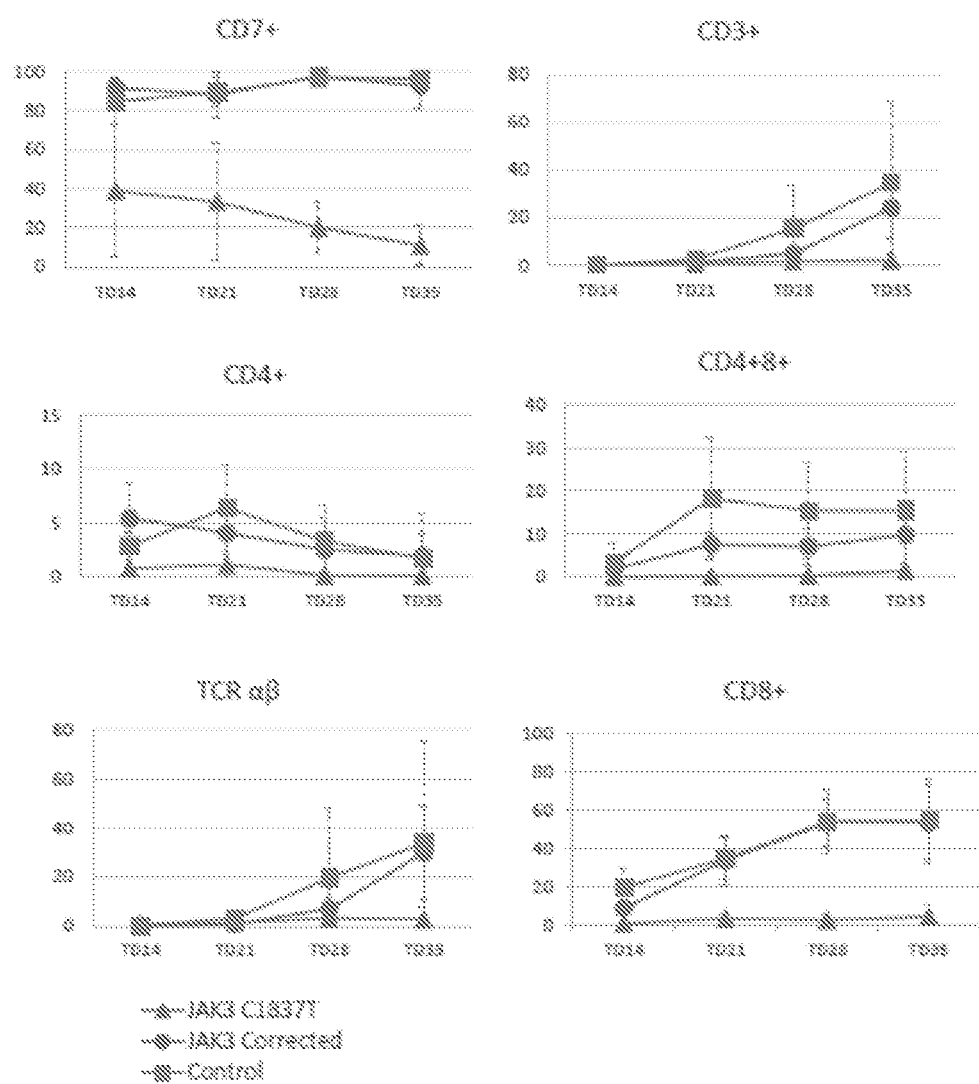
FIGS. 4A-4C show in vitro differentiation of JAK3 corrected patient iPSCs produces T cells with phenotypic and functional characteristics of mature T cells.

JAK3-Deficient Human T Cells Express Low Levels of BCL2 and Die at an Early Developmental Stage IPSCs were generated from skin keratinocytes (Chang et al., 2009) of a SCID patient homozygous for a C>T nucleotide substitution in exon 14 of the JAK3 gene. This mutation replaces a CGA codon (arginine at 613) with a TGA stop codon (p.R613X). As described above, the four-month-old patient presented with a T−B+NK-clinical phenotype. To determine whether this SCID phenotype can be recapitulated in vitro, differentiation of patient-specific iPSCs to T lymphocytes using a two-step OP9 and OP9-DL4 system (Chang et al., 2014) was attempted. JAK3-deficient iPSCs grew at a rate comparable to control iPSCs derived from healthy donors, and these iPSCs efficiently differentiated into CD34+ hematopoietic progenitors (HPs) on OP9 stromal cell monolayers. However, when the JAK3-deficient, iPSC-derived CD34+ HPs were plated on OP9-DL4 stromal cell monolayers, T-cell differentiation was absent compared to controls (FIG. 1). No CD3+ T cells or CD3-CD16+CD56+ NK cells were observed (FIG. 1A), and no CD4+CD8+ double positive (DP), CD4+ single positive (SP), or CD8+ single positive (SP) T cells were detected (FIG. 1B). Jak3 knockout (KO) mice have a small thymus due to a block in thymocyte differentiation at the CD4-CD8-double negative (DN) stage prior to productive TCR rearrangement. To further understand the developmental defects resulting from a JAK3 mutation in humans, T lineage commitment and maturation of JAK3-deficient cells compared to normal JAK3 WT controls was assayed. IPSC-derived CD34+ cells were plated on OP9-DL4 monolayers, and cells were harvested and analyzed for lymphocyte markers at T-cell induction day (TD) 14, 21, 28 and 35 (FIG. 4A). In normal controls, $1.2 \times 10^7$ CD7+ cells (84% of cells counted in the lymphoid gate) were generated at TD14 from $1\text{-}2\times 10^6$ CD34+ cells. T cell markers CD4, CD8, CD3 and TCR αβ were sequentially detected upon T cell maturation. At TD35, more than 50% of the population was CD8 SP cells. In JAK3-deficient cells, only $4.5 \times 10^4$ CD7+ cells (38.9% of cells counted in lymphoid gate) were generated at TD14 from $1\text{-}2\times 10^6$ CD34+ cells. The number of CD7+ cells decreased during extended culture and T cell markers CD3, CD4, CD8 and TCR αβ were not significantly expressed. During the transition through early T cell progenitors (ETPs), the CD4−CD8−(DN) to CD4+ CD8+ (DP) stages are directed by precise activation and repression of specific transcription factors. In control cells, the silencing of PU.1 and induction of GATA3 and BCL11 B (FIG. 1C) suggest that these cells proceed to the onset of T lineage commitment (DN2 to DN3) followed by TCR rearrangement. In contrast, in JAK3-deficient cells PU.1 accumulates and GATA3 and BCL11 B levels are reduced (FIG. 1C). These data suggest that human JAK3-deficient cells arrest before or at the DN2 stage, which is similar to the stage at which T cells die in Jak3 KO mice. Interestingly, human JAK3-deficient cells may express sufficient RAG1, RAG2 and PTCRA (FIG. 1C) to perform TCR rearrangement, but the cells do not survive long enough to proceed to this important developmental stage. These profound defects in lymphocyte development of JAK3-deficient cells can be explained by the absence of IL-7 signaling which plays an important role in lymphoid progenitor survival and differentiation. IL-7/JAK3 signaling maintains thymocyte homeostasis by regulating the BCL2 family of apoptotic regulators. Thymocytes and peripheral T cells from Jak3 KO mice have a high apoptotic index in part through selectively elevating BAX, a pro-apoptotic factor, and by reducing expression of BCL2, an anti-apoptotic factor. Similarly, in these studies, an increase in apoptosis of in vitro-derived human JAK3-deficient cells compared to controls at TD10 (9% to 2.2%) and TD17 (7% to 1.9%) (FIG. 2A). Consistent with this phenotype, BAX levels were increased and BCL2 levels were reduced in JAK3-deficient cells compared to controls (FIG. 2B). Forced expression of Bcl2 rescues T, but not B or NK cell development in γc-deficient mice (Kondo et al., Immunity 7: 155-162 (1997)). Transplantation of Jak3 KO mice with Bcl2-expressing Jak3 KO bone marrow cells also improves peripheral T cell numbers (Wen et al., Molecular and cellular biology 21: 678-689 (2001)). To determine whether overexpression of BCL2 will rescue T cell developmental defects of human JAK3-deficient cells, in vitro-derived, JAK3-deficient CD34+ cells were transduced with a lentivirus containing a BCL2-2 A-GFP polycistron driven by EF1a promoter. After transduction, CD34+ cells were plated on OP9-DL4 monolayers and assayed for NK and T cell markers at TD 28. No CD3-CD16+CD56+ NK cells were found in GFP-(JAK3−; BCL2 low) or GFP+ cells (JAK3−; BCL2+) (FIG. 2C). These findings suggest that BCL2 released the blockage at the DN stage in JAK3-deficient cells. Interestingly, a second developmental arrest was evident at the DP stage; no further differentiation of CD8+CD4+ DP positive cells was observed in GFP+ cells (FIG. 2C). In summary, the studies described above demonstrate that human SCID phenotypes can be recapitulated in vitro with patient-derived iPSCs. JAK3 deficiency results in proliferative defects in DN thymocytes. Forced expression of BCL2 enhances survival of DN cells, which further differentiate into DP thymocytes. Nevertheless, DP thymocytes fail to mature to SP T cells, and this defect may result from the absence of IL7/ JAK3 signaling.

Figure 3A:
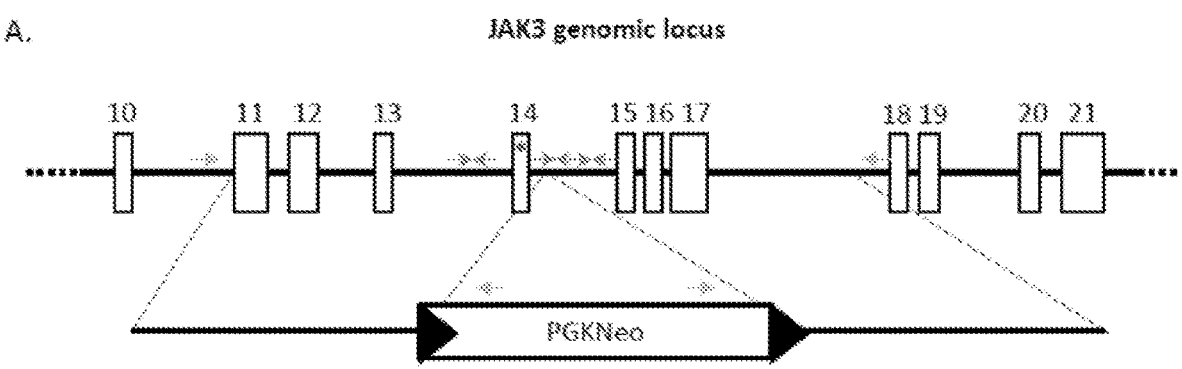
FIGS. 3A-3D show that CRISPR/Cas9 enhanced correction of the JAK3 C1837 T mutation in patient-specific iPSCs.
Figure 3B:
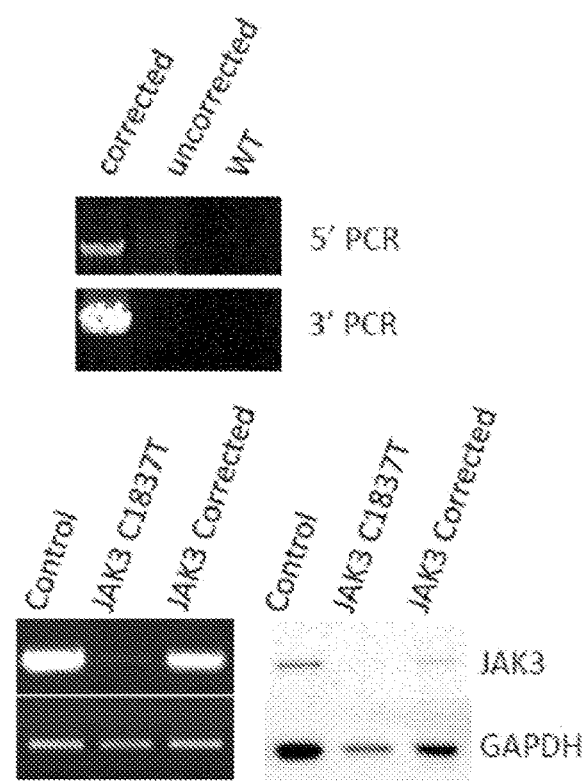
Figures 3C, 3D:
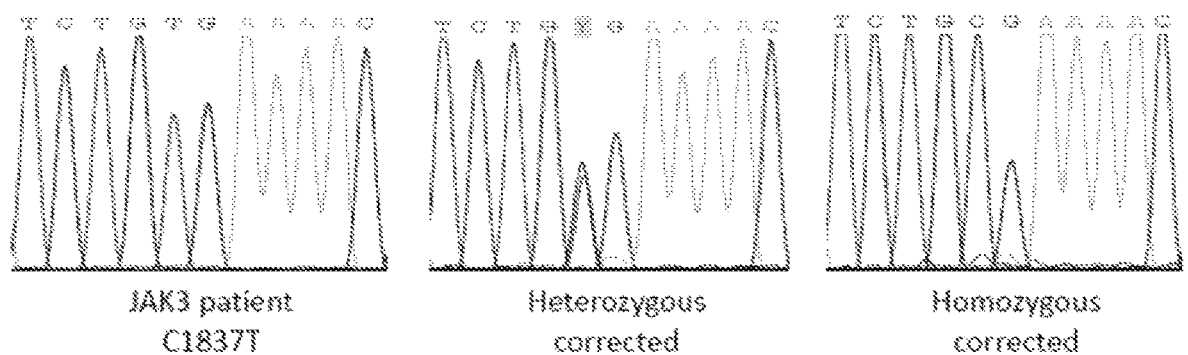

Correction of the JAK3 Deficiency in SCID hiPSCs by CRISPR/Cas9 Enhanced Gene Replacement To determine whether normal T cell development can be restored in JAK3-deficient SCID patient cells, the JAK3 mutation was corrected in iPSCs by CRISPR/Cas9 enhanced gene replacement. Six guide RNAs within introns upstream and downstream of exon 14 were designed to target wtCas9 or nCas9 near the C1837 T mutation, and a correction template was used for gene replacement (FIG. 3A). IPSCs were nucleofected with two plasmids expressing the D10 A Cas9 nickase and paired guide RNAs or a single plasmid expressing wild-type Cas9 and a single guide RNA. Cells were grown in medium containing G418 for 2 weeks post nucleofection. Individual colonies were picked, expanded, and genotyped by PCR (FIG. 3B Top). The efficiency of CRISPR/Cas9-mediated JAK3 gene correction is shown in FIG. 3C. Three clones from WT Cas9+gRNA #1, 3 clones from WT Cas9+gRNA #2 and 6 clones from Cas9 nickase +paired gRNAs #1 and #2 were further verified by Sanger sequencing. In 12 sequenced clones, 2 homozygous corrected clones (1 clone from Cas9 nickase +paired gRNA #1 and #2, and 1 clone from WT Cas9+gRNA #1) and 10 heterozygous corrected clones were identified (FIG. 3D). Restoration of JAK3 gene expression was demonstrated by RT-PCR (JAK3 mRNA) (FIG. 3B; lower left panel) and western blot (JAK3 protein) (FIG. 3B; lower right).

Specificity of CRISPR/Cas9 Directed JAK3 Correction

The potential for off-target, CRISPR/Cas9 directed genome modifications raises some concerns about the use of this approach for therapy in humans. In cancer cell lines, relatively high levels of off-target mutagenesis by Cas9-gRNAs have been described. To determine the specificity of CRISPR/Cas9 directed JAK3 correction in human SCID iPSCs, Whole genome sequencing was performed before and after gene replacement. The genomes of two heterozygous and one homozygous corrected clones were sequenced. The two heterozygous clones were corrected with gRNA #2+wild type Cas9, and the homozygous clone was corrected with gRNA #1+gRNA #2+nickase Cas9 (D10A). The 20-base CRISPR guide sequences were mapped to the human reference genome, allowing up to 3 mismatches in order to identify possible off-target sites. These sites were then analyzed for variations in the iPSC samples following CRISPR/Cas9 directed gene replacement. WGS analysis of one homozygous and two heterozygous corrected iPSC lines demonstrated that no mutations (SNVs nor indels) were introduced into the predicted off-target sites, suggesting a strong specificity for the CRISPR/Cas9 directed gene replacement.

Restoration of T Cell Development after CRISPR/Cas9 Directed JAK3 Correction

Figure 4B:
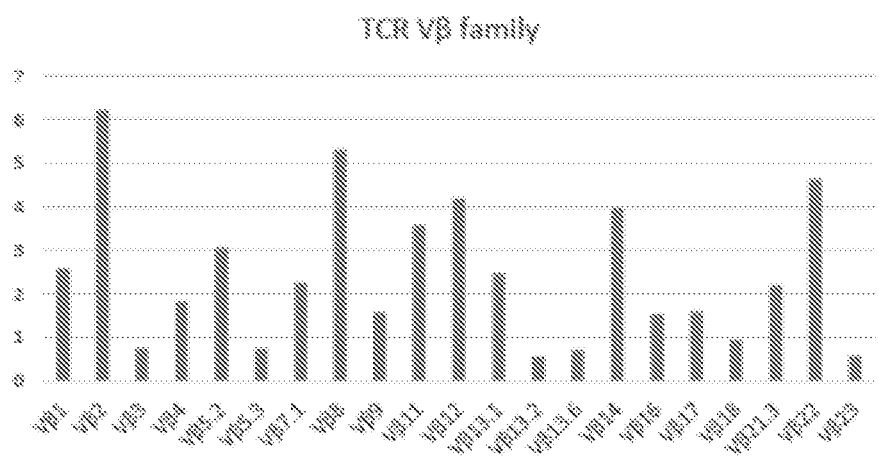
Figure 4C:
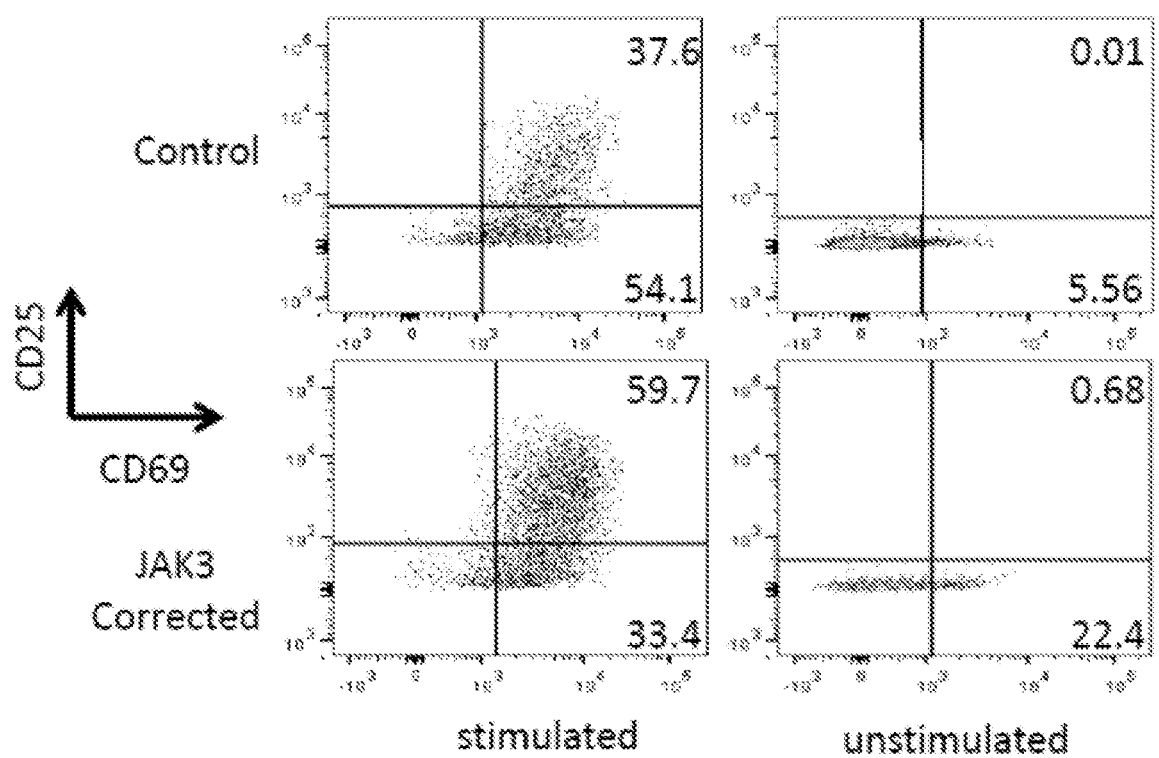

To determine whether T cell development is restored after JAK3 gene correction, T cell lineage commitment and maturation were assayed. T cell differentiation sequentially passes through intermediates observed in vivo: CD34+ CD7+ T/NK committed stage; CD7+CD4+CD8-immature, SP stage; CD4+CD8+ DP stage; and finally, CD3+CD8+ TCRαβ mature stage. Mature T cells are polyclonal, proliferate, and secrete cytokines in response to mitogens. Therefore, JAK3 corrected hiPSCs were differentiated into hematopoietic progenitors on OP9 monolayers, and CD34+ cells were positively selected on anti-CD34 magnetic beads. These cells were plated on OP9-DL4 monolayers, and nonadherent cells were analyzed for lymphocyte markers at TD14, 21, 28 and 35 (FIG. 4). Similar to control cells, 1-2×10⁶ CD34+ JAK3 corrected cells differentiated into 4.7×10⁶ CD7+ cells (91% of cells counted in lymphoid gate) at TD14. After further differentiation to TD21, TD28 and TD35, T cell maturation markers CD3, CD4, CD8 and TCR αβ were abundantly observed (FIG. 4A). To determine whether TCR rearrangement is reestablished in JAK3-corrected T cells, TCR Vβ typing was performed by flow cytometry and summarized in FIG. 4B. JAK3-corrected T cells expressed all the Vβ segments that we tested (19 of 25); therefore, a broad TCR repertoire was restored. Finally, the integrity of the TCR signaling pathway, a surrogate of T cell function, in JAK3-corrected T cells, was examined by measuring cell surface activation markers following anti-CD3/ CD28 stimulation. On Day 3 post-stimulation, the percentage of CD3+CD25+CD69+ T cells increased from 0.68% to 59.7% in JAK3-corrected T cells similar to the increase observed in control cells (0.01% to 37.6%) (FIG. 4C). These data and results described above demonstrate that correction of the JAK3 C1837 T (p.R613X) mutation by CRISPR/Cas9 enhanced gene replacement in an in vitro iPSC model system restores normal T cell development with the capacity to produce functional, mature T cell populations with a broad TCR repertoire.

In humans, the phenotype of lymphocytes in the peripheral blood of SCID patients has been well described, but studies on critical steps of lymphoid commitment and thymocyte development have been difficult to perform. Access to bone marrow and thymocyte samples from untreated patients with SCID is challenging since these conditions are rare and infants typically present with life-threatening infections requiring urgent HSC transplantation to survive. The strategy described herein for studying human SCID bypasses these restrictions; large numbers of hematopoietic progenitors can be produced from patient specific iPSCs in vitro, and the mechanisms responsible for immunodeficiency can be precisely determined. Demonstrated herein is that T cell development in human JAK3-deficient SCID is completely blocked before or at the CD4-CD8-(DN2) stage. Interestingly, forced expression of BCL2 enhances survival of DN cells, which further differentiate into DP thymocytes. However, DP thymocytes fail to mature to SP T cells, and this defect may result from the absence of IL7/ JAK3 signaling. It is also demonstrated that correction of the human JAK3 mutation by CRISPR/Cas9 enhanced gene replacement restores the differentiation potential of early T cell progenitors. Corrected progenitors are capable of producing NK cells and mature T cell populations expressing a broad TCR repertoire. Whole-genome sequencing analysis of one homozygous and two heterozygous corrected iPSC lines demonstrates that no mutations (SNVs nor indels) are introduced into the predicted off-target sites, suggesting a strong specificity for the CRISPR/Cas9 directed gene replacement.

Figure 5:
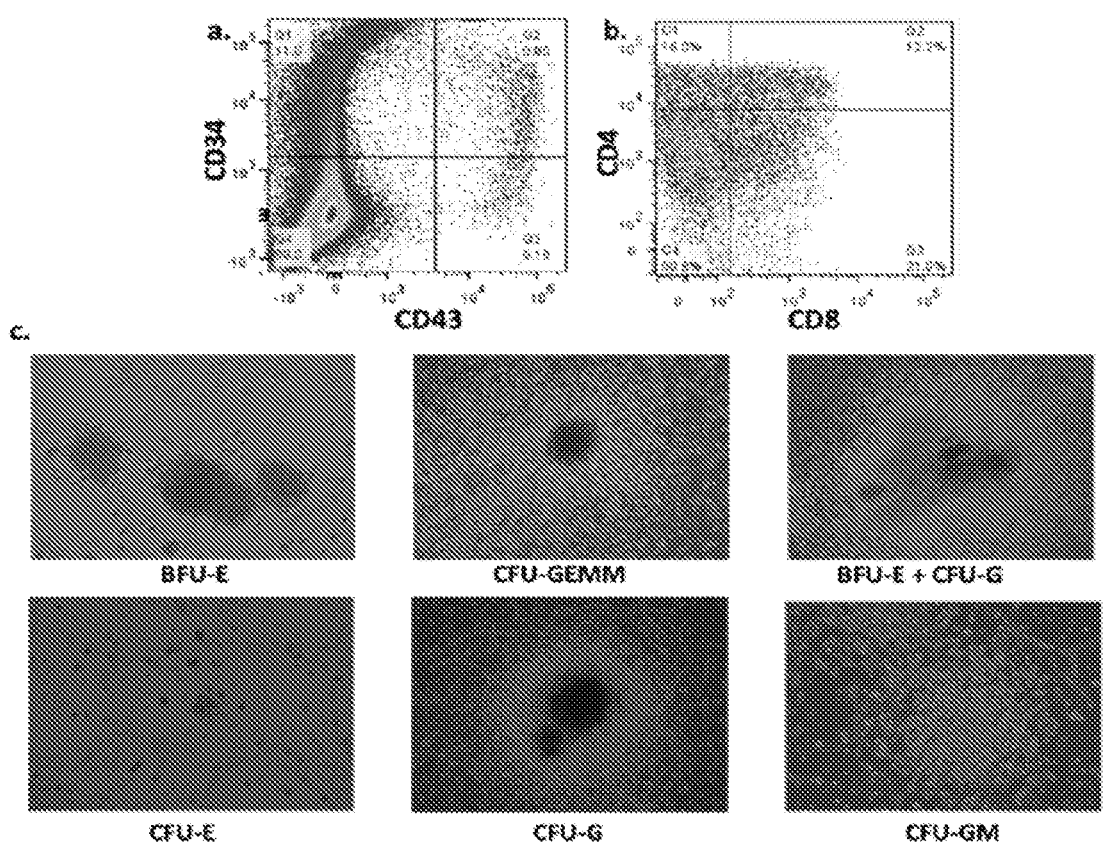
FIGS. 5A-5C show in vitro generation of CD34+HSCs from hiPSCs by co-culture with human bone marrow stromal cells (hMSC). Human iPSCs were cultured on hMSCs for 18 days before analysis for hematopoietic markers, CD34 and CD43 (Figure A). CD34+ cells were purified on beads and differentiated into T cells (Figure B), erythroid and myeloid cells (Figure C). To generate T cells, purified CD34+ cells were plated on OP9-DL4 cells for 3 to 4 weeks. For the CFC assay to generate myeloid and erythroid cells, purified CD34+ cells were plated in MethoCult H4434 Classic medium according to the manufacturer's protocol. These data demonstrate that hiPSC can be efficiently differentiated into multipotent HSC after co-culture on hMSC.
Figure 6:
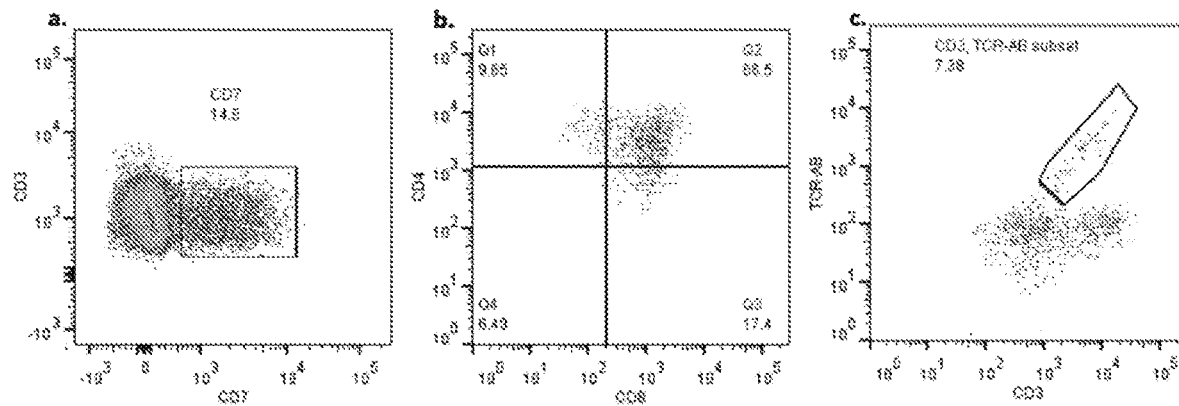
FIG. 6A-6C show in vitro generation of T cells by culturing hiPSC derived CD34+ cells with hMSC-DL4. To generate CD7+ T progenitor cells, hiPSC derived CD34+ cells were co-cultured on hMSC-DL4 for 3 to 4 weeks (FIG. 6A). When CD7+ cells from FIG. 6A were purified on magnetic beads and co-cultured on OP9-DL4, fully mature CD4+/CD8+/CD3+/TCR-αβ+ cells were produced in 10 days or less (Figures B and C). These data demonstrate that hiPSC can be efficiently differentiated into CD7+ lymphoid progenitors after co-culture on hMSC-DL4.
Figure 7:
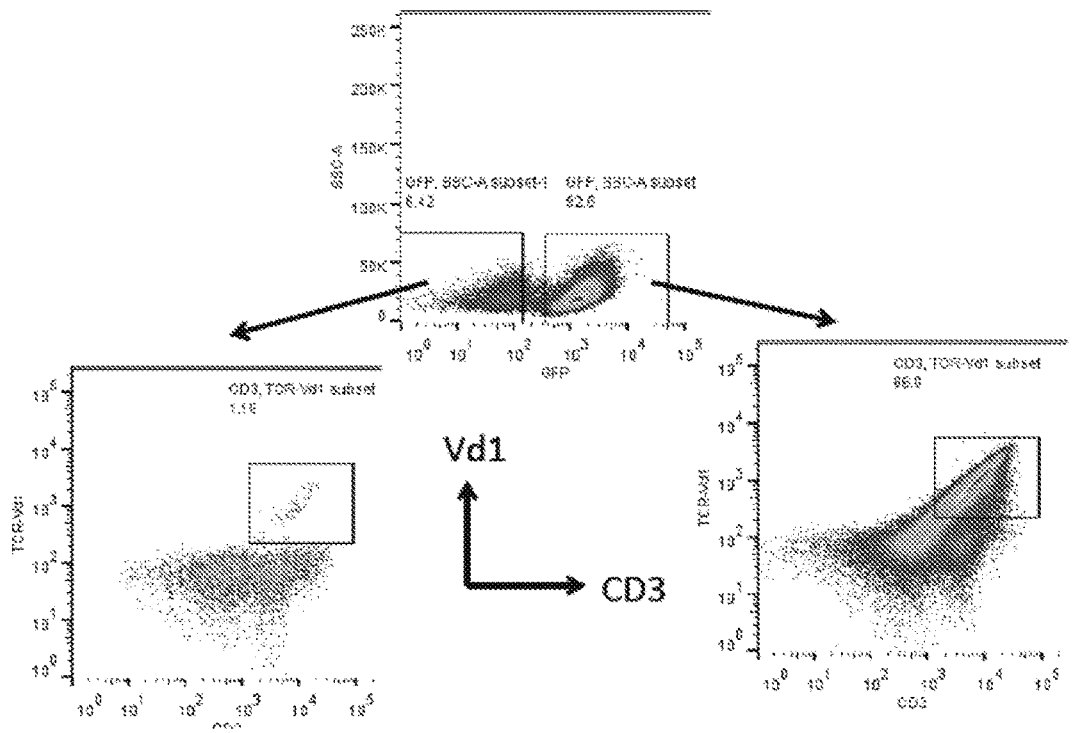
FIG. 7 shows in vitro generation of γδ T cells from hiPSC. Human iPSC were transduced with a lentiviral vector carrying a pre-rearranged human V γδ1 cDNA linked with a 2 A-GFP cDNA fragment. After co-culture with OP9 for 18 days, hiPSC derived CD34+ cells were purified on magnetic beads. These cells were subsequently plated on OP9-DL4 cells for T cell differentiation. Cells were harvested at Day 32 and T cell surface markers were analyzed by FACS. The GFP+ population represents Vδ1-2 A-GFP lentiviral transduced cells. A high percentage of these GFP positive cells expressed Vδ1 (66%). A low percentage of GFP negative cells expressed Vδ1 (1%). These results demonstrate that Vδ T cells expressing recombinant T Cell Receptors (TCR) can be efficiently produced from genetically modified iPSC. Production of Vδ T cells expressing recombinant T Cell Receptors (TCR) specific for tumor antigens provides a powerful cellular therapy for many types of cancer.

In the methods described herein, CD34+ HSCs can be generated from hiPSCs by co-culturing with human bone marrow stromal stem (hMSC) cells (See FIG. 5). The HSCs produced by this method from patient-specific iPSC after gene correction/modification could be transplanted back into the patient to treat diseases such as sickle cell disease (SCD), SCID or cancer. In the methods described herein, T cells can be generated by culturing hiPSC derived CD34+ cells by co-culturing the hiPSC derived CD34+ cells with hMSC-DL4 (See FIG. 6). HSCs produced by this method from patient-specific iPSC after correction/modification could be transplanted back into the patient to treat diseases. The T cells can comprise γδ T cells. As shown in FIG. 7, γδ T cells expressing recombinant T cell receptor (TCR) can be efficiently produced from genetically modified iPSC. Production of γδ T cells expressing TCR specific for tumor antigens provide a cellular therapy for cancer.

Example 2

Correction of a Mutation Associated with Sickle Cell Anemia by CRISPR/Cas9 Enhanced Gene Replacement Vector Construction The human codon optimized *S. pyogenes* Cas9 with both N-terminal and C-terminal nuclear localization sequences (nls-Cas9-nls) were PCR cloned from px330 vector (Addgene ID: 42230) into a modified pET-28 b (EMD Biosciences) vector with a His$_6$-SUMO tag at the N-terminus. A gene block cassette containing a short linker peptide followed by a supercharged GFP with a net charge of +36 and a 23 amino acid influenza virus hemagglutinin HA-2 variant peptide INF7 (GLFEAIEGFIENGWEGMIDGWYG)(SEQ ID NO: 50) was codon optimized for *E. coli* and synthesized (IDT DNA) and cloned to fuse with the C-terminus of the nls-Cas9-nls. An HIV-TAT peptide (YGRKKRRQRRRPPQ))(SEQ ID NO: 51) coding sequence was also synthesized (IDT DNA) and cloned to fuse with the N-terminus of the nls-Cas9-nls.

Protein Overexpression and Purification

The pET-SUMO-scCas9 plasmid was transformed into *E. coli* strain Rosetta™ 2 (DE3) cells (EMD Millipore, Billerica, Mass.) in LB medium. The cells were grown at 37° C. until the optical density reached 0.6 at 600 nm. Induction of protein overexpression was achieved by adding 0.5 mM isopropyl-1-thio-β-D-galactopyranoside (IPTG) and culturing overnight at 18° C. in a shaker. The harvested cells were re-suspended in Ni-binding buffer (20 mM Tris-HCl pH 8.0, 1.5 M NaCl, 25 mM imidazole and 0.2 mM TCEP) and lysed by Emulsiflex C3 high pressure homogenizer (Avestin). Polyethyleneimine (PEI) with final concentration of 0.4% was added into the cleared lysate to precipitate the nucleic acids. The proteins in the supernatant after centrifugation was then precipitated by ammonium sulfate to remove the PEI and re-dissolved in the Ni-binding buffer. The proteins were first purified by a HisTrap nickel affinity column (GE Healthcare) followed by overnight digestion with SUMO protease Ulp1 at 4° C. The cleaved His-SUMO tag was then removed via a second HisTrap column. The flow though containing the scCas9 protein was diluted to reach the final NaCl concentration of 0.5 M and purified on a HiTrap Heparin column (GE Healthcare) by gradient elution with buffer containing 20 mM Tris-HCl pH 8.0, 2.0 M NaCl, and 0.2 mM TCEP. The eluted scCas9 protein was further purified by a size exclusion column Superdex 200 16/600 (GE Healthcare) in gel filtration buffer (20 mM Tris-HCl pH 8.0, 0.5 M NaCl, and 0.2 mM TCEP), sterilized by passing through a 0.22 µm filter and concentrated by an Amicon Centrifugal Unit (EMD Millipore) with 100 kDa cutoff. The concentrated protein was quantified by UV spectrophotometer and flash frozen in liquid nitrogen.

Guide RNA Preparation

Template DNA for sgRNA transcription was generated by PCR with primer set adding a T7 promoter and a polyA sequences. sgRNA was in vitro transcribed by T7 RNA polymerase using T7 Ribomax Express System (Promega, Madison, Wis.) according to the manufacturer's manual. The transcribed RNA was purified by phenol: chloroform extraction, ethanol precipitation and followed by column purification with MEGAclear™ Transcription Clean-Up Kit (Ambion, Austin, Texas). The purified gRNA was quantified by UV spectrophotometer and stored in −80° C. freezer.

Single-Stranded DNA Donors

Single-stranded DNA (ssODN) donors were synthesized by IDT DNA as shown below.

| Single-stranded Donor DNAs for HBB sickle correction | |
| --- | --- |
| HBB-T2-ssODN | ATCCACGTTCACCTTGCCCCACAGGGCAGTAACGGCAGAC TTCTCCtCAGGAGTCAGGTGCACCATGGTGTCTGTTTGAG GTTGCTAGTGA (SEQ ID NO: 52) |
| HBB-T2-ssODN-wobble | CTTCATCCACGTTCACCTTGCCCCACAGGGCAGTAACGGC AGAtTTtTCCtCAGGAGTCAGGTGCACCATGGTGTCTGTT TGAGGTTGCTAGTGA (SEQ ID NO: 53) |

Cell Culture

Human sickle patient iPSC were derived from skin fibroblasts and were maintained on Matrigel (BD) in mTeSR™1 medium (Stem Cell Technologies, Vancouver, Calif.) with penicillin/streptomycin.

scCas9-sgRNA-ssODN Complex Preparation and Nucleofection 1/10 volume of 10× PBS was added into sgRNA to reach 1× final concentration. The sgRNA was annealed on PCR thermo cycler with slow decreasing of temperature from 95° C. to 4° C. After annealing, scCas9 protein was added into the sgRNA with a 1:1.5 protein-to-RNA molar ratio and mixed quickly by tapping the tube until all the transient precipitation was gone. The mixture was incubated in room temperature for 10 minutes in dark. Then, 1 molar ratio amount of ssODN was added into the mixture and incubated for additional 10 minutes in dark to form the scCas9-sgRNA-ssODN complex.

One day before nucleofection, cells were detached by Accutase (Stem Cell Technologies) and 1×10⁶ cells /well cells were seeded on a 6-well plate with 10 µM Rock inhibitor (Y-27632) (EMD Millipore). For each experiment, 5×10⁵ hsIPSCs were resuspended as single cells in 100µl supplemented Human Stem Cell Nucleofector Solution 1 (Lonza) and scCas9-sgRNA-ssODN complex was then mixed with the cell solution. The cells were nucleofected with program A-023 using a Nucleofector II device (Lonza, Basel, Switzerland). The efficiency of HBB genome correction was analyzed by ddPCR two days post nucleofection.

Detection of Sickle Correction by ddPCR

The cells nucleofected with the scCas9-sgRNA-ssODN complex were lysed by prepGEM Tissue DNA extraction reagent (ZyGEM, Hamilton, NZ) following manufacturer's manual and 1:3 diluted with water. In a 22 µl ddPCR reaction, 11 µl 2×ddPCR mix (Bio-rad) was mixed with 1 ul each of 5 µM allele-specific FAM or VIC Taqman probes set forth below, 0.2 µl each of a 100 µM forward and reverse primer, and 8.6 µl diluted genomic DNA. Droplets were generated by QX200 Droplet Generator (Bio-rad, Hercules, Calif.) according to the manufacturer's manual. The reaction mix was then transferred into a 96-well PCR plate and the PCR was performed on a standard thermal cycler (Bio-rad). The program for PCR was: Step 1: 95° C. 10 min; Step 2: 95° C. 30 s; Step 3: 55° C. 1 min; repeat steps 2-3 for 39 times; Step 4: 98° C. 10 min; Step 5: 8° C. hold. After PCR was done, the plate was then analyzed by QX200 Droplet Reader (Bio-rad).

| T7-sgRNA transcription template primers | | |
| --- | --- | --- |
| T7-T2-F | TAATACGACTCACTATAGGGTAACGGCAGACTTCTCCAC (SEQ ID NO: 54) | |
| T7-polyA-R | AAAAAGCACCGACTCGGTGCC (SEQ ID NO: 55) | |

| Taqman Probes: | | |
| --- | --- | --- |
| HBB-wb-FAM-TM | FAM-TCCTGaGGAaAAAaT-MGB (SEQ ID NO: 56) | |
| HBB-wt-FAM-TM | FAM-TGACTCCTGAGGAGAA-MGB (SEQ ID NO: 57) | |
| HBB-sk-VIC-TM | VIC-ACTCCTGTGGAGAAG-MGB (SEQ ID NO: 58) | |

| ddPCR Primers: | | |
| --- | --- | --- |
| R196 | HBB-TaqM-f2 | CAGAGCCATCTATTGCTTACATTTG (SEQ ID NO: 59) |
| R197 | HBB-TaqM-r1 | GGCCTCACCACCAACTTCAT (SEQ ID NO: 60) |

Figure 8:
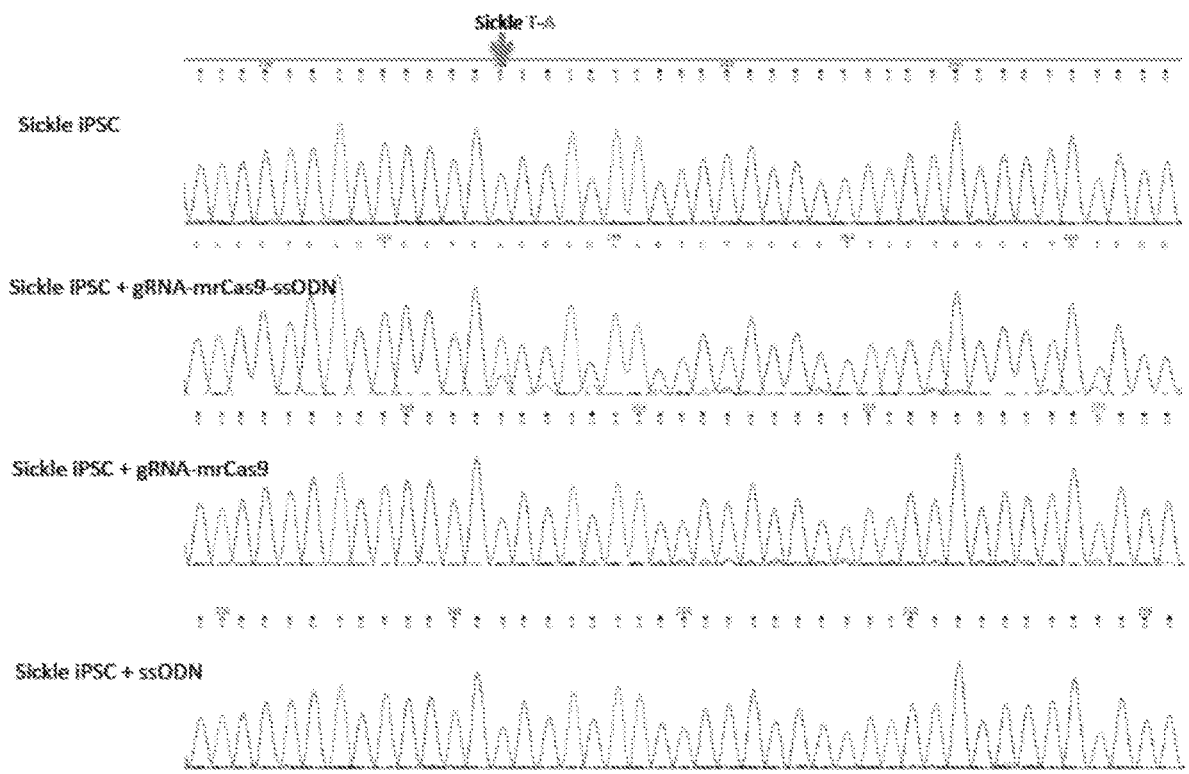
FIG. 8 shows that a correction complex including guide RNA, a modified Cas9 and a single stranded oligonucleotide donor sequence (ssODN) can correct a sickle cell mutation. The complex was introduced into sickle iPSC by nucleoporation, and 2 days later genomic DNA was analyzed by digital PCR (ddPCR) and sequenced. Over 65% of the cells contained at least one corrected gene. The results were confirmed as follows. Two days after introduction of the correction complex, the cells were plated in culture dishes, and 43 individual iPSC colonies were isolated. Genomic DNA was isolated from these colonies and the beta-globin gene was sequenced. Sixty-five percent of the colonies contained at least one corrected beta-globin gene (S corrected to A).

As set forth above, a complex that includes a guide RNA (gRNA), modified recombinant Cas9 protein (mrCas9) and a single-stranded oligodeoxyribonucleotide (ssODN) can be introduced into human stem cells or derivatives thereof to correct a single base mutation that causes disease. Table 1 and FIG. 8 illustrate results from the introduction of a sickle cell correction complex (gRNA-mrCas9-ssODN) into induced Pluripotent Stem Cells (iPSC) derived from skin cells of a sickle cell patient. IPSCs were derived as described in Example 1. The correction complex was introduced into sickle iPSC by nucleoporation and 2 days later genomic DNA was analyzed by digital PCR, using the primers set forth above, and sequenced. Over 65% of the cells contained at least one corrected gene. One corrected gene is sufficient to cure the disease. The results were confirmed as follows. Two days after introduction of the correction complex, the cells were plated in culture dishes, and 43 individual iPSC colonies were isolated. Genomic DNA was isolated from these colonies and the beta-globin gene was sequenced. Sixty-five percent of the colonies contained at least one corrected beta-globin gene (S corrected to A).

TABLE 1

|  | gRNA-mrCas9-ssODN | |
| --- | --- | --- |
| Pooled ddPCR result (2-day) | 68.6% | |
| Total colonies picked after 2 weeks | 48 | |
| Mixed colonies | 5 | |
| Total single colonies | 43 | |
| A/A | 14 | 32.6% |
| A/S | 4 | 9.3% |
| S/S | 3 | 7.0% |
| A/indel | 10 | 23.3% |
| S/indel | 6 | 14.0% |
| Indel/indel | 6 | 14.0% |
| Clones with at least 1 allele corrected | 28 | 65.1% |
| Clones with indels | 22 | 51.2% |
| Clones with genome modification | 40 | 93.0% |
| Total number of alleles | 86 | |
| Total "A" alleles (corrected) | 42 | 48.8% |
| Total "S" alleles uncorrected | 16 | 18.6% |
| Total "indel" alleles | 28 | 32.6% |
| A:(A + S) *comparable to ddPCR result | 42/58 = 72.4% | |
| HR:NHEJ (A:indel) ratio | 1.50 | |

Figure 9:
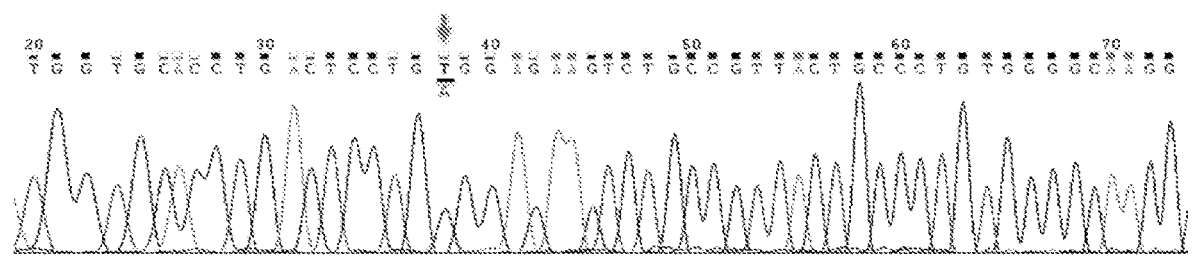
FIG. 9 shows that introduction of a sickle cell correction complex (gRNA-modified recombinant Cas9-ssODN) into patient primary bone marrow CD34+ cells can correct a sickle cell mutation. After twelve days of in vitro differentiation, DNA was analyzed by digital PCR (ddPCR) and sequenced. Approximately equal amounts of betaA and betaS mRNA were observed.
Figure 10:
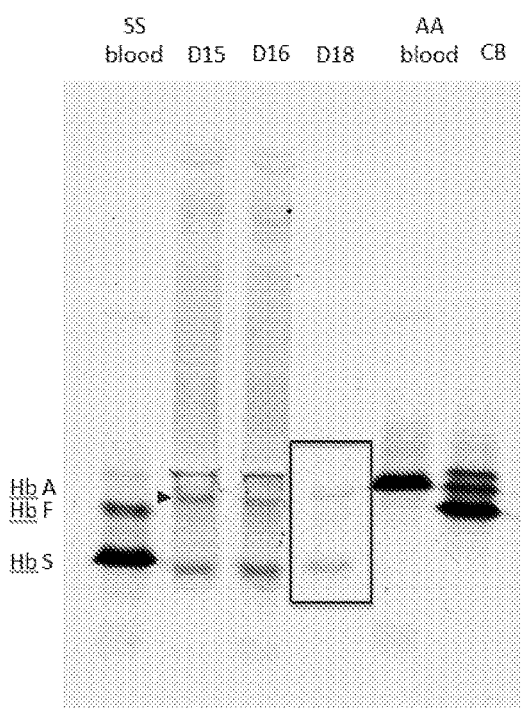
FIG. 10 is an isoelectric focusing (IEF) gel of in vitro differentiated red blood cells from the corrected sickle patient CD34+ cells of FIG. 9, showing an HbA (normal hemoglobin) to HbS (hemoglobin with sickle cell mutation) ratio of about 1:3, which is sufficient to inhibit sickling and treat sickle cell anemia.

Similar studies were performed with patient primary bone marrow CD34+ cells. The protocol was as follows. Bone marrow was obtained from a sickle patient by an IRB approved protocol. CD34+ cells were purified on a Miltenyi anti-CD34+ beads (Miltenyi, Bergisch Gladbach, Germany). The cells were nucleoporated with the complex prepared as described above. After nucleoporation, the cells plated in methycult and BFU-E, CFU-E and CFU-GEMM colonies were picked after two weeks and analyzed for corrected alleles. Table 2 and FIG. 9 illustrate results from the introduction of a sickle cell correction complex (gRNA-mrCas9-ssODN) into patient primary bone marrow CD34+ cells. After twelve days of in vitro differentiation, DNA was analyzed by digital PCR (ddPCR) and sequenced. Approximately equal amounts of betaA and betaS mRNA were observed (See FIG. 9). Immediately after nucleoporation, some of the cells were culture in erythroid differentiation medium for up to eighteen days and enucleated red blood cells were analyzed for HbA. An isoelectric focusing (IEF) gel of in vitro differentiated red blood cells from the corrected sickle patient CD34+ cells showed an HbA (normal hemoglobin) to HbS (hemoglobin with sickle cell mutation) ratio of about 1:3, which is sufficient to inhibit sickling and treat the disease (See FIG. 10).

TABLE 2

| Complex for nucleofection | Cas9wt-36GFP-T2-ssODN | |
| --- | --- | --- |
| Nucleofection Program | P4 DN-100 | |
| BFU-E/CFU-E/GEMM colonies picked on D10 and D15 | 21/23/7 | |
| Total colonies* | 51 | |
| A/A | 2 | 4% |
| A/S | 4 | 8% |
| S/S | 19 | 37% |
| A/indel | 5 | 10% |
| S/indel | 15 | 29% |
| Indel/indel | 6 | 12% |
| Clones with at least 1 allele corrected | 11 | 22% |
| Clones with indels | 24 | 47% |
| Clones with genome modification | 29 | 57% |
| Total number of alleles | 102 | |
| Total "A" alleles (corrected) | 13 | 13% |
| Total "S" alleles (uncorrected) | 57 | 56% |
| Total "indel" alleles | 32 | 31% |
| A:(A + S) *comparable to ddPCR result | 13/70 = 18.6% | |
| HR:NHEJ (A:indel) ratio | 0.41 | |

Sequences

SEQ ID NO: 1
TAACGGCAGACTTCTCCAC

SEQ ID NO: 2
GTAACGGCAGACTTCTCCACGTTTTAGAGCTAGAAATAGCAAGTTAAAATAAGG
CTAGTCCGTTATCAACTTGAAAAAGTGGCACCGAGTCGGTGCTTTTTTT

SEQ ID NO: 3
Cas9-supercharged GFP construct
mdykdhdgdykdhdidykddddkmapkkkrkvgihgvpaadkkysigldigtnsvgwavitdeykvpskkfkvlgntdrh
sikknligallfdsgetaeatrlkrtarrrytrrknricylqeifsnemakvddsffhrleesflveedkkherhpifgnivdevayhek
yptiyhlrkklvdstdkadlrliylalahmikfrghfliegdlnpdnsdvdklfiqlvqtynqlfeenpinasgvdakailsariskarrl
enliaqlpgekknglfgnlialslgltpnfksnfdlaedaklqlskdtydddldnllaqigdqyadlflaaknlsdaillsdilrvnteitk
aplsasmikrydehhqdltllkalvrqqlpekykeiffdqskngyagyidggasqeefykfikpilekmdgteellvklnredllrk
qrtfdngsiphqihlgelhailrrqedfypflkdnrekiekiltfripyyvgplargnsrfawmtrkseetitpwnfeevvdkgasaqs
fiermtnfdknlpnekvlpkhsllyeyftvyneltkvkyvtegmrkpaflsgeqkkaivdllfktnrkvtvkqlkedyfkkiecfds
veisgvedrfnaslgtyhdllkiikdkdfldneenedilediviltltlfedremieerlktyahlfddkvmkqlkrrrytgwgrlsrkli
ngirdkqsgktildflksdgfanrnfmqlihddsltfkediqkaqvsgqgdslhehianlagspaikkgilqtvkvvdelvkvmgr
hkpeniviemarenqttqkgqknsrermkrieegikelgsqilkehpventqlqneklylyylqngrdmyvdqeldinrlsdydv
dhivpqsflkddsidnkvltrsdknrgksdnvpseevvkkmknywrqllnaklitqrkfdnltkaergglseldkagfikrqlvetr
qitkhvaqildsrmntkydendklirevkvitlksklvsdfrkdfqfykvreinnyhhandaylnavvgtalikkypklesefvyg
dykvydvrkmiakseqeigkatakyffysnimnffkteitlangeirkrplietngetgeivwdkgrdfatvrkvlsmpqvnivkk
tevqtggfskesilpkrnsdkliarkkdwdpkkyggfdsptvaysylvvakvekgkskklksvkellgitimerssfeknpidfle
akgykevkkdliiklpkyslfelengrkrmlasagelqkgnelalpskyvnflylashyeklkgspedneqkqlfveqhkhyldei
ieqisefskrviladanldkvlsaynkhrdkpireqaeniihltltlnlgapaafkyfdttidrkrytstkevldatlihqsitglyetridls
qlggdkrpaatkkaggakkkksgsgnsgsaskgerlfrgkvpilvelkgdvnghkfsvrgkgkgdatrgkltlkficttgklpv
pwptlvttltygvqcfsrypkhmkrhdffksampkgyvqertisfkkdgkyktraevkfegrtlvnriklkgrdfkekgnilghkl
rynfnshkvyitadkrkngikakfkirhnvkdgsvqladhyqqntpigrgpvllprnhylstrsklskdpkekrdhmvllefvtaa
gikhgrderyk

| Sequences |
|---|
| SEQ ID NO: 4<br>TAT-Cas9-supercharged GFP construct<br>ygrkkrrqrrrppqaggsmdykdhdgdykdhdidykddddkmapkkkrkvgihgvpaadkkysigldigtnsvgwavitd<br>eykvpskkfkvlgntdrhsikknligallfdsgetaeatrlkrtarrrytrrknricylqeifsnemakvddsffhrleesflveedkkh<br>erhpifgnivdevayhekyptiyhlrkklvdstdkadlrliylalahmikfrghfliegdlnpdnsdvdklfiqlvqtynqlfeenpin<br>asgvdakailsarlsksrrlenliaqlpgekknglfgnlialslgltpnfksnfdlaedaklqlskdtydddldnllaqigdqyadlflaa<br>knlsdaillsdilrvnteitkaplsasmikrydehhqdltlllkalvrqqlpekykeiffdqskngyagyidggasqeefykfikpilek<br>mdgteellvklnredllrkqrtfdngsiphqihlgelhailrrqedfypflkdnrekiekiltfripyyvgplargnsrfawmtrkseet<br>itpwnfeevvdkgasaqsfiermtnfdknlpnekvlpkhsllyeyftvyneltkvkyvtegmrkpaflsgeqkkaivdllfktnrk<br>vtvkqlkedyfkkiecfdsveisgvedrfnaslgtyhdllkiikdkdfldneenediledivltltlfedremieerlktyahlfddkv<br>mkqlkrrrytgwgrlsrklingirdkqsgktildflksdgfanrnfmqlihddsltfkediqkaqvsgqgdslhehianlagspaikk<br>gilqtvkvvdelvkvmgrhkpeniviemarenqttqkgqknsrermkrieegikelgsqilkehpventqlqneklylyylqngr<br>dmyvdqeldinrlsdydvdhivpqsflkddsidnkvltrsdknrgksdnvpseevvkkmknywrqllnaklitqrkfdnltkaer<br>gglseldkagfikrqlvetrqitkhvaqildsrmntkydendklirevkvitlksklvsdfrkdfqfykvreinnyhhahdaylnavv<br>gtalikkypklesefvygdykvgdvrkmiakseqeigkatakyffysnimnfffkteitlangeirkrplietngetgeivwdkgrdf<br>atvrkvlsmpqvnivkktevqtggfskesilpkrnsdkliarkkdwdpkkyggfdsptvaysylvvakvekgkskklksvkell<br>gitimerssfeknpidfleakgykevkkdliiklpkyslfelengrkrmlasagelqkgnelalpskyvnflylashyeklkgsped<br>neqkqlfveqhkhyldeiieqisefsskrviladanldkvlsaynkhrdkpireqaeniihlftltnlgapaafkyfdttidrkrytstke<br>vldatlihqsitglyetridlsqlggdkrpaatkkagqakkkkgsgsngsssgsaskgerlfrgkvpilvelkgdvnghkfsvrgkgk<br>gdatrgkltlkficttgklpvpwptlvttltygvqcfsrypkhmkrhdffksampkgyvqertisfkkdgkyktraevkfegrtlvnr<br>iklkgrdfkekgnilghklrynfnshkvyitadkrkngikakfkirhnvkdgsvqladhyqqntpigrgpvllprnhylstrsklsk<br>dpkekrdhmvllefvtaagikhgrderykggsggsvdglfeaiegfiengwegmidgwyg |

What is claimed is:

1. A method of making tumor-specific T-cell precursor cells comprising introducing into a population of T-cell precursor cells a complex comprising:

a. a guide RNA (gRNA) comprising a first nucleotide sequence that hybridizes to a target DNA in the genome of the T cell precursor cells and a second nucleotide sequence that interacts with a CRISPR-Cas9 nuclease;

b. a recombinant CRISPR-Cas9 nuclease operably linked to a superpositively charged protein, wherein the CRISPR-Cas9 nuclease comprises an RNA-binding portion that interacts with the second nucleotide sequence of the gRNA, wherein the CRISPR-Cas9 nuclease specifically binds and cleaves the target DNA to create a double stranded break, wherein the positively supercharged protein is a superpositively charged green fluorescent protein (GFP) that has an overall positive charge from about +5 to about +40, and wherein the superpositively charged protein is operably linked to the carboxy-terminus of the CRISPR-Cas9 nuclease; and c. a donor nucleic acid sequence comprising a third nucleotide sequence that encodes a chimeric antigen receptor (CAR) and a fourth nucleotide sequence that hybridizes to a genomic sequence flanking the double stranded break in the target DNA, wherein the complex is introduced into the T-cell precursor cells, by nucleoporation, under conditions that allow homology-directed repair (HDR) and integration of the third nucleotide sequence into the target DNA to form modified T-cell precursor cells that express the CAR, and wherein the ratio of homology-directed repair to nonhomologous end joining in the population of T-cell precursor cells is at least 0.5.

2. The method of claim 1, wherein the cells are selected from the group consisting of hematopoietic stem cells or pluripotent stem cells.

3. The method of claim 2, wherein the pluripotent stem cells are induced pluripotent stem cells.

4. The method of claim 1, wherein the recombinant CRISPR-Cas9 nuclease operably linked to a superpositively charged protein further comprises a trans-activating transcriptional activator (TAT) peptide operably linked to the amino-terminus of the CRISPR-Cas-9 nuclease.

5. The method of claim 1, wherein the molar ratio of gRNA to CRISPR-Cas9 nuclease operably linked to a superpositively charged protein to donor nucleic acid is from about 1:1:1 to about 1.5:1:1.

6. The method of claim 1, wherein at least 5% of the population of T-cell precursor cells are modified by HDR to form modified T-cell precursor cells that express the CAR.

7. The method of claim 1, further comprising isolating the modified T-cell precursor cells.

8. The method of claim 7, further comprising culturing the modified T-cell precursor cells.

9. The method of claim 8, further comprising culturing the modified T-cell precursor cells under conditions that promote differentiation of the modified T-cell precursor cells into T cells that express the CAR.

10. A method of making tumor-specific T-cell precursor cells comprising introducing into a population of T-cell precursor cells a complex comprising:

a. a guide RNA (gRNA) comprising a first nucleotide sequence that hybridizes to a target DNA in the genome of the T cell precursor cells and a second nucleotide sequence that interacts with a CRISPR-Cas9 nuclease;

b. a recombinant CRISPR-Cas9 nuclease operably linked to a superpositively charged protein, wherein the CRISPR-Cas9 nuclease comprises an RNA-binding portion that interacts with the second nucleotide sequence of the gRNA, wherein the CRISPR-Cas9 nuclease specifically binds and cleaves the target DNA to create a double stranded break, wherein the positively supercharged protein is a superpositively charged green fluorescent protein (GFP) that has an overall positive charge from about +5 to about +40, and wherein the superpositively charged protein is operably linked to the carboxy-terminus of the CRISPR-Cas9 nuclease; and c. a donor nucleic acid sequence comprising a third nucleotide sequence that encodes a chimeric antigen receptor (CAR) and a fourth nucleotide sequence that hybridizes to a genomic sequence flanking the double stranded break in the target DNA, wherein the complex is introduced into the T-cell precursor cells, by nucleoporation, under conditions that allow homology-directed repair (HDR) and integration of the third nucleotide sequence into the target DNA to form modified T-cell precursor cells that express the CAR, and wherein at least 5% of the population of T-cell precursor cells are modified by HDR to form modified T-cell precursor cells that express the CAR.

11. The method of claim 10, wherein the cells are selected from the group consisting of hematopoietic stem cells or pluripotent stem cells.

12. The method of claim 11, wherein the pluripotent stem cells are induced pluripotent stem cells.

13. The method of claim 10, further comprising isolating the modified T-cell precursor cells.

14. The method of claim 13, further comprising culturing the modified T-cell precursor cells.

15. The method of claim 14, further comprising culturing the modified T-cell precursor cells under conditions that promote differentiation of the modified T-cell precursor cells into T cells that express the CAR.

* * * * *